United States Patent [19]

Tosa et al.

[11] Patent Number: 5,538,691
[45] Date of Patent: Jul. 23, 1996

[54] REACTION VESSEL FOR OPTICAL MEASUREMENT

[75] Inventors: Kaori Tosa, Kusatsu; Yoshiyuki Hama; Kouichi Yamamoto, both of Shiga; Ryuuji Akiyama, Kusatsu; Masakazu Yoshida, Kusatsu; Hiroshi Yagi, Kusatsu; Kazuhisa Shigemori, Shiga; Tomomi Sakamoto, Sakurai, all of Japan

[73] Assignee: Daikin Industries, Ltd., Osaka, Japan

[21] Appl. No.: 199,155

[22] PCT Filed: Jun. 25, 1993

[86] PCT No.: PCT/JP93/00873

§ 371 Date: Mar. 23, 1994

§ 102(e) Date: Mar. 23, 1994

[87] PCT Pub. No.: WO94/00761

PCT Pub. Date: Jan. 6, 1994

[30] Foreign Application Priority Data

Jun. 26, 1992 [JP] Japan ............................. 4-169720
Sep. 8, 1992 [JP] Japan ............................. 4-239120
Nov. 11, 1992 [JP] Japan ............................. 4-301189

[51] Int. Cl.⁶ ............................................. G01N 21/03
[52] U.S. Cl. .................... 422/102; 422/82.05; 422/82.08; 422/82.11; 356/246; 250/227.14; 385/12
[58] Field of Search .................... 422/102, 104, 422/58, 82.05, 82.11, 82.08; 436/164, 165, 810; 356/246; 250/227.14, 361 C; 385/12

[56] References Cited

U.S. PATENT DOCUMENTS 3,718,439  2/1973  Rosse et al. ............................. 422/102
3,883,308  5/1975  Matte ........................................ 23/259
3,939,350  2/1976  Kronick et al. .......................... 250/365
3,994,594  11/1976 Sandrock et al. ........................ 356/246
4,251,159  2/1981  White ....................................... 356/246
4,746,179  5/1988  Dahne et al. ........................... 350/96.10
4,979,821  12/1990 Schutt et al. ............................. 356/246
5,186,896  2/1993  Bouchée et al. ........................... 422/72

FOREIGN PATENT DOCUMENTS 49-112687  10/1974  Japan.
52-29271   3/1977   Japan.
1-282447   11/1989  Japan.
3-72236    3/1991   Japan.
3-72263    3/1991   Japan.
4-5569     1/1992   Japan.
4-225144   8/1992   Japan.
4-225145   8/1992   Japan.

*Primary Examiner*—Jill Warden
*Assistant Examiner*—Long V. Le
*Attorney, Agent, or Firm*—Beveridge, DeGrandi, Weilacher & Young

[57] ABSTRACT

An apparatus for optical measurement is formed as a one-piece molding. The apparatus has a reaction vessel and pre-treatment vessels, at least part of the partitioning wall between the both serves as an optical waveguide body, and a light absorber vessel is formed adjacent the reaction vessel (24). Simplification of the process of manufacture thus is attained. With a light absorber accommodated in the light absorber vessel, (25), reaction components of excitation light and other noise light components that are propagated through the optical waveguide body can be sufficiently attenuated to improve the S/N ratio of the optical measurement.

18 Claims, 19 Drawing Sheets

REACTION VESSEL FOR OPTICAL MEASUREMENT

FIELD OF THE INVENTION

This invention relates to apparatuses for optical measurement and, more particularly, to an apparatus for optically determining conditions in the neighborhood of the surface of an optical waveguide according to measurement light of extremely low light intensity compared to the intensity of excitation light. One example is an apparatus for fluorescent immunity measurement, in which excitation light is introduced into an optical waveguide to excite a label fluorescent material present in the neighborhood of the optical waveguide surface for determining whether immunity is present or the extent thereof, if any, according to excited fluorescent light.

PRIOR ART

A known method of optical measurement has been well known in uses a slab type optical waveguide for exciting only label fluorescent light present in the neighborhood of the surface of the optical waveguide with an evanescent component tidal is emitted slightly from the optical waveguide and determines whether immunity is present or the extent thereof, if any, according to the excited fluorescent light. FIG. 23 shows an apparatus for implementing this method. The apparatus has a slab type optical waveguide 91 with all integral test solution chamber 92 formed on one surface. Excitation light emitted from a laser or the like (not shown) is led through a dichroic mirror 93 to the optical waveguide 91, and fluorescent light that is radiated from a label fluorescent material is led through the optical waveguide 91 to be reflected by the dichroic mirror 93 and passed through an optical filter 94 so as to be incident on a detector 95.

Where this structure is used, antibodies 96 are preliminarily attached to kite surface of the optical waveguide 91. Antigens 97 in the test solution are received in the antibodies 96. Further, fluorescent label antibodies 98 that are labeled by the fluorescent body are received in the antigens 97. The quantity of the received fluorescent label antibodies 98 is thus determined according to the quantity of the antigens 97 present in the test solution. The evanescent component that is obtained by introducing the excitation light into the optical waveguide 91 excites only label fluorescent bodies 98a of the received fluorescent label antibodies 98 to cause radiation of fluorescent light. Thus, the intensity of the radiated fluorescent light is proportional to time quantity of the antigens 97 in the test solution. The fluorescent light is led through the optical waveguide 91.

Thus, the sole fluorescent light that has been guided through the optical waveguide 91 is reflected by the dichroic mirror 93 to be incident on the detector 95 with the excitation light component blocked by the optical filter 94. In this way, it is possible to determine whether immunity is present or the extent thereof, if any.

However, in the fluorescent immunity measurement apparatus of the above construction, it is usually necessary to dilute the antigens 97, i.e., the liquid under test, and mix the antigens 97 and fluorescent label antibodies 98 before accommodating the liquid under test and the fluorescent label antibodies 98. The operations of dilution and miming are done by using a pre-treatment vessel which is preliminarily assembled in the measurement apparatus or by using a consumable pre-treatment vessel unit which is manufactured in correspondence to the reaction vessel.

Where the pre-treatment vessel preliminarily assembled in the apparatus is used for the diluting and mixing operations, the involved mechanism is usually extremely complicated. Therefore, it is highly possible that the operations for the diluting and mixing are complicated. In addition, since the pre-treatment vessel is used repeatedly, residual matter that may remain in the pre-treatment vessel due to unsatisfactory washing may be introduced into the liquid under test, thus leading to errors in the measurement.

Where the consumable pre-treatment vessel unit manufactured in correspondence to the reaction vessel is used for the dilution and the mixing a considerable cost increase is inevitable because the pre-treatment vessel is formed alone. In addition, since the reaction vessel and pre-treatment vessel are a one-to-one correspondence relation, it takes time to prepare pre-treatment vessels corresponding in number to the number of reaction vessels.

In order to preclude the above inconveniences, the inventors have thought, as shown in FIG. 24, to produce a reaction vessel 84 accommodating a slab type waveguide 80. Specifically, the opposite ends of the slab type waveguide 80 are each provided with an integral light incidence/emission prism 81. Meanwhile, a pair of pre-treatment vessels 82 are formed such that they are spaced apart a predetermined distance via a connecting section 83. The light incidence/emission prisms 81 are pressure fitted from above in the space between the opposed ends of the paired pre-treatment vessels 82, and portions of the light incidence/emission prisms 81 which lave no optical influence on the measurement are engaged with the opposed ends noted above.

With the optical measurement apparatus shown in FIG. 24, however, adhesive that is coated in advance on the opposed ends noted above foe bonding the light incidence/emission prisms 81 and the ends to one another, can get out of position when the prisms 81 are fitted. It is thus necessary to coat the adhesive again after the completion of the pressure fitting, thus leading to cumbersomeness in the operation of manufacturing the optical measurement apparatus. Besides, deviation of the angle of the light incidence/emission prisms relative to the axis of light incidence is possible due to assembling errors. In this case, the fluorescent immunity measurement signal fluctuates, as shown in FIG. 25. Further, since the slab type optical waveguide is bare at the time of the assembling, it is highly possible that fingerprints and dust are attached. Further, when discharging the liquid under test from the reaction vessel 84 before accommodating fluorescent label antibodies, the liquid under test may remain in a lower space of the slab type waveguide 80 or the like. In such a case, with the fluorescent label antibodies poured into the reaction vessel 84, the concentration of the fluorescent label antibodies is reduced by the residual liquid under test to result in time reduction of the accuracy of time fluorescent immunity measurement.

Further, even by coating the adhesive again after the completion of the pressure fitting, there is no guarantee that the top surface of the pre-treatment vessels 82 and that of the light incidence/emission prisms 81 are flush with one another. Therefore, when the top opening of the reaction vessel 84 is sealed after accommodating a preservation liquid therein in order to hold the slab type optical waveguide 80 in a humidified state during transportation and storage, the seal may become imperfect. Further, since the excitation light that is introduced into the slab type optical waveguide 80 through one of the light incidence/emission prisms 81 is emitted through the other light incidence/ emission prism 81, it is impossible to dispose a reagent vessel or the like on the extension of the slab type optical waveguide 80.

DISCLOSURE OF THE INVENTION

An object of the invention is to extremely facilitate the manufacture of optical measurement apparatus as a whole and also dispense with the positioning of the slab type optical waveguide and the bonding operation.

Another object of the invention is to extremely simplify operations necessary for the optical measurement inclusive of the operation of dilution and mixing.

A further object of the invention is to increase the accuracy of the optical measurement.

To attain the above objects of the invention, there is provided an optical measurement apparatus, which comprises a plurality of vessels formed together as a or monolithic molding, at least one of the vessels being a reaction vessel, the reaction vessel or vessels regularly facing at least one of the other vessels, time regularly facing side wall of the reaction vessel or vessels also serving as a slab type optical waveguide. Thus, the optical measurement apparatus can be obtained simply by injection molding or time like. In addition, since at least one of the vessels regularly faces the reaction vessel or vessels and the regularly facing side wall of the reaction vessel or vessels also serves as a slab type optical waveguide, it is possible to prevent the inconveniences which result when an operator's fingers or the like touch the slab type optical waveguide.

Further, the slab type optical waveguide is disposed substantially vertically and, with settling and deposition of disturbing matter containing in the liquid under test, most of the reaction surface of the slab type optical waveguide can be held free from the influence of the deposited disturbing matter. Thus, it is possible to permit satisfactory optical measurement.

The slab type optical waveguide may be one with antigens, antibodies or haptens that are preliminarily attached to at least one side surface. In this case, it is possible to permit optical determination of whether immunity is present and the extent thereof, if any.

Suitably, the slab type optical waveguide is disposed in an inclined state such that the reaction vessel has a narrowed bottom. In this case, it is possible to readily separate molding dies after injection molding or the like. In addition, it is possible to improve the smoothness of the slab type waveguide surface.

Further, suitably some of the vessels other than the reaction vessel or vessels are pre-treatment vessels. In this case, when carrying out optical measurement with the optical measurement apparatus obtained by injection molding or the like, the liquid unter test, diluting solution, etc. may be accommodated in some of the plurality of pre-treatment vessels. By so doing, it is possible to permit the operation of diluting the liquid under test to be easily attained by using a desired pre-treatment vessel and also permit the optical measurement to be easily attained by pouring the solution after completion of necessary pre-treatment into a reaction vessel.

In this case, a plurality of pre-treatment vessels may be provided such that they include a reagent vessel and/or a diluting solution vessel, whereby the same functions as above are attainable.

In the above cases, suitably one of the pre-treatment vessels is a reagent vessel, which stores a fluorescent material and is disposed such as to regularly face none of the reaction vessel side walls. In this case, when the fluorescent material in the reagent vessel is excited by excitation light propagated while being totally reflected in proceeding through the slab type optical waveguide, the effects of fluorescent light emitted from the fluorescent material on the reaction vessel can be extremely reduced to eventually increase the sensitivity of the optical measurement.

Suitably, the optical measurement apparatus has a seal applied to cover at least the reagent and dilution solution vessels. This arrangement permits the reagent and dilution solution in time respective vessels to be held reliably in the vessels even when the optical measurement apparatus is vibrated during storage, transport, etc. Of course a series of operation necessary for optical measurement may be performed by separating the seal.

Further, the slab type optical waveguide has a light incidence/emission prism provided at one end for introducing excitement light into it in order for the excitement light to be propagated while being totally reflected and also for emitting signal light containing optical measurement information, and suitably a light absorber vessel is disposed such that it corresponds to the other end of the slab type optical waveguide. In this case, the light absorber contained in time light absorber vessel can absorb fluorescent light or the like, which is generated by the slab type optical waveguide as noise component with respect to time measurement light, with propagation of the excitement light introduced into the waveguide through the excitement light introduction prism. It is thus possible to extremely reduce fluorescent light or time like returning toward time excitement light introduction prism. Of course, the light absorber contained in the light absorber vessel can absorb the introduced excitement light, thus extremely reducing excitement light which is reflected by other portions than The slab type optical waveguide to be introduced into the reaction vessel. It is thus possible to permit measurement light substantially free from a noise component to be emitted from the excitement light introduction prism, thus extremely increasing the accuracy of the optical measurement. Further, the optical absorber need not be coated on the slab type optical waveguide but may be merely accommodated in the light absorber vessel. That is, no particular consideration is needed for any range of coating of the light absorber. In addition, since the light absorber is not touched by the liquid under test, it is possible to extremely broaden the scope of applications of the light absorber.

Further, time slab type optical waveguide has a light incidence/emission prism provided at one end for introducing excitement light into it in order for the excitement light to be propagated while being totally reflected and also for emitting signal light containing optical measurement information, and suitably it also has a total reflection prism provided at the other end for emitting the excitement light in a direction at a predetermined angle with respect to its optical axis. In this case, when the excitement light that has been introduced into the slab type optical waveguide through the excitement light introduction prism is emitted, it is totally reflected by the total reflection prism, and thus it is possible to let the direction of extension of the slab type optical waveguide and time direction of the excitement light emission be sufficiently different. The reagent vessel of the like thus can be disposed on the extension of the slab type optical waveguide, and it is possible to increase the degree in freedom of vessel disposition. Further, it is possible to readily cope with an increase of the number of vessels. Further, when the slab type optical waveguide itself emits fluorescent light or the like which is a noise component with respect to the measurement light, that which is returning toward the excitement light introduction prism can be extremely reduced, thus eventually increasing the accuracy of the optical measurement.

Further, the slab type optical waveguide has a light incidence/emission prism provided at one end for introducing excitement light into it in order for the excitement light to be propagated while being totally reflected, and suitably light blocking means for blocking light is provided in a predetermined area adjacent an excitement light introduction area of the light incidence/emission prism. In this case, it is possible to reliably prevent excitement light from being introduced through the area adjacent the excitement light introduction area of the excitement light introduction prism. In addition, it is possible to reliably prevent emission of scattered light, generated light, etc., in other areas than the slab type optical waveguide and the surface neighborhood. Thus, the proportion of noise light component contained in the measurement light can be extremely reduced to extremely increase the accuracy of the optical measurement.

Further, of the side walls of the reaction vessel, that which extends substantially perpendicular to and located on the excitement light introduction side of the slab type optical waveguide and/or that which extends substantially parallel to the slab type optical waveguide, are/is suitably coated with a black paint. In this case, when excitement light intrudes into the reaction vessel as it is introduced into the slab type optical waveguide, the coated black paint can absorb the noise component due to the intruding excitement light, thus reducing the radiation of the noise component to the outside of the reaction vessel (i.e., to the outside on the excitement light introduction side). Further, when excitement light intrudes into the reaction vessel as it is led by scattering or the like to side walls facing the slab type optical waveguide after having been propagated through the waveguide, the coated black paint can absorb the intruding excitement light. It is thus possible to reduce the excitement light component intruding into the reaction vessel and hence reduce the noise component due to this excitement light.

Further, suitably the optical measurement apparatus further comprises a light detector for detecting signal light emitted from the slab type optical waveguide and also an analyzer for analyzing immunity reactions according to detection signals from the light detector. In this case, with excitement light introduced in the slab type optical waveguide for propagation through the same while being totally reflected, signal light indicative of the optical character of the neighborhood of the slab type optical waveguide surface is emitted from the waveguide. This signal light can be detected by the light detector for immunity reaction analysis in the analyzer according to detection signals from the light detector.

BEST FORMS OF CARRYING OUT THE INVENTION

Figure 1:
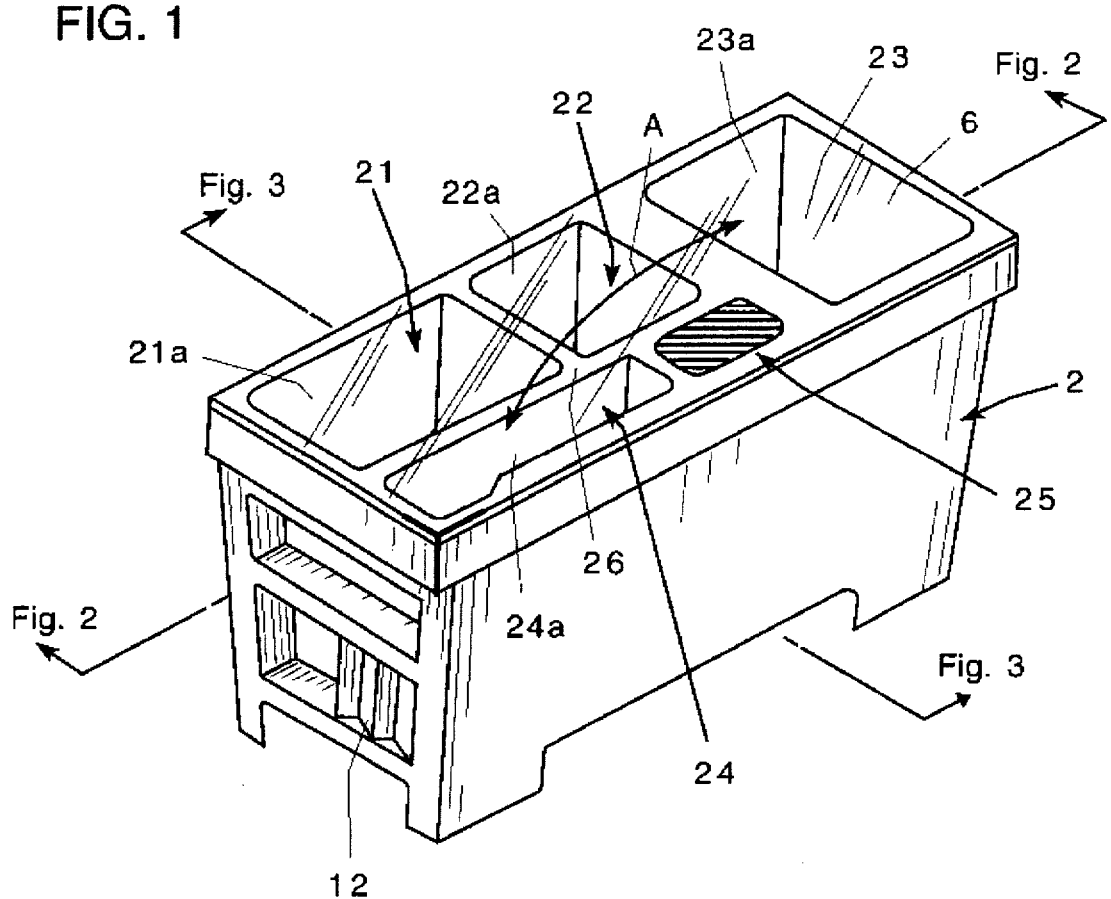
FIG. 1 is a perspective view showing a fluorescent immunity measurement apparatus as an embodiment of the optical measurement apparatus according to the invention.
Figure 2:
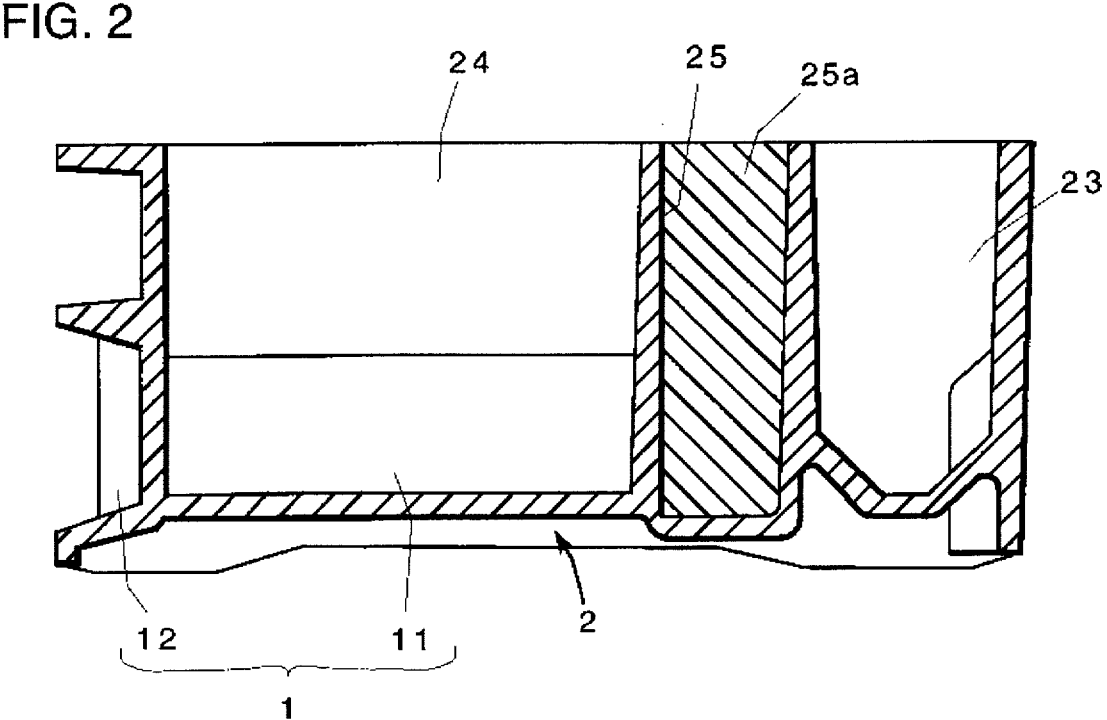
FIG. 2 is a sectional view taken along line II—II in FIG. 1.
Figure 3:
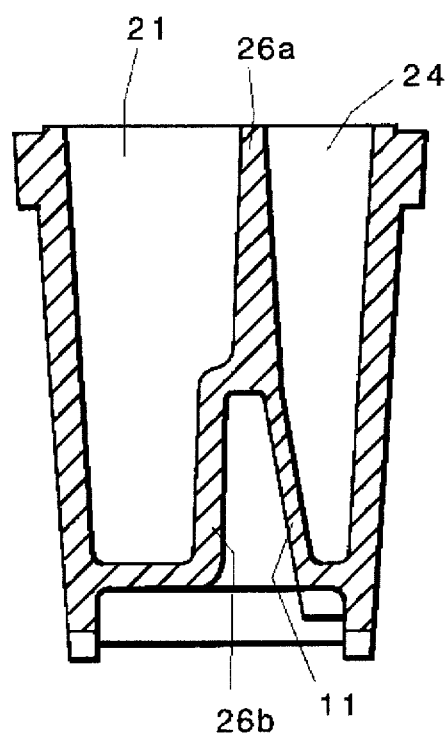
FIG. 3 is a sectional view taken along line III—III in FIG. 1.

FIG. 1 is a perspective view showing a fluorescent immunity measurement apparatus as an embodiment of the optical measurement apparatus according to the invention. FIGS. 2 and 3 are sectional views taken along lines II—II and III—III in FIG. 1, respectively. In FIG. 1, the internal structure is not shown. This fluorescent immunity measurement apparatus has two pre-treatment vessels 21 and 22, which are provided in predetermined portions of a casing 2 in a side-by-side arrangement in the longitudinal direction of the casing, and a reaction vessel 24 regularly facing the entire pre-treatment vessel 21 and substantially one half of the pre-treatment vessel 22. A light absorber vessel 25 is provided such that it regularly faces the rest of the pre-treatment vessel 22 and is located on an extension of the reaction vessel 24. A further pre-treatment vessel 23 is provided such that it regularly faces the pre-treatment vessel 22 and light absorber vessel 25. Time pre-treatment vessels 21 and 22, reaction vessel 24 and light absorber vessel 25, are defined by a partitioning member 26. The partitioning member 26 has an upper half portion 26a having a predetermined thickness. Its lower half portion includes a partitioning wall 26b exclusive for the pre-treatment vessels 21 and 22 and a partitioning wall 11 exclusive for the reaction vessel 24 and the light absorber vessel 25. The partitioning wall 11 has highly accurately flat opposite surfaces and also serves as an optical waveguide body 11 of the slab type optical waveguide 1. A narrow space is defined between the partitioning walls 26b and 11, and it can prevent such inconvenience as attachment of fingerprints or dust to the optical waveguide 11 caused by being touched by fingers or hands. An excitation light introduction prism 12 is provided such that it faces the reaction vessel side end of the optical waveguide body 11. The casing 2, which has the pre-treatment vessels, reaction vessel, light absorber vessel, optical waveguide body, excitation light introduction prism, etc., is formed as a one-piece molding by injection molding or the like. The light absorber vessel 25 is filled with a light absorber 25a, which is composed of a black paint, a silicone resin, etc. The light absorber may not be black in case where the excitation light is not white light. The slab type optical waveguide 11 is not exactly vertical but is slightly inclined from the vertical so that the reaction vessel 24 is narrow at the bottom and broad in an upper portion. This arrangement permits surface polishing to be attained highly accurately and also permits polishing dust to be easily removed. Further, it permits die separation to be easy at the time of the molding. Further, since the reaction vessel 24 formed in the above way is progressively broader as one goes up from the bottom and also free from any stepped portion, it is possible to remove liquid under test that has been distributed into the vessel substantially perfectly before distribution of a solution containing fluorescent label antibodies: It is thus possible to reliably preclude the inconvenience of reaction of the fluorescent label antibody concentration. Further, at least a portion of the side wall of the reaction vessel 24 is made transparent. The movement of a pipette or the like thus can be confirmed with the transparent portion of the vessel when distributing the liquid under test or the like.

After the fluorescent immunity measurement apparatus having the above construction has been obtained, a solution is accommodated in a pertinent pre-treatment vessel, a preservation liquid for preserving antibodies 3 is accommodated in the reaction vessel 24, and the top openings 21a to 24a of the pre-treatment and reaction vessels 21 to 24 are covered by mounting a seal member 6. Thus, leakage of liquid during transport, storage, etc. can be reliably prevented. In this case, the seal member 6 is attached to the optical measurement apparatus which is in the form of a one-piece molding, it is possible to reliably prevent such inconvenience that the seal becomes imperfect.

Figure 4:
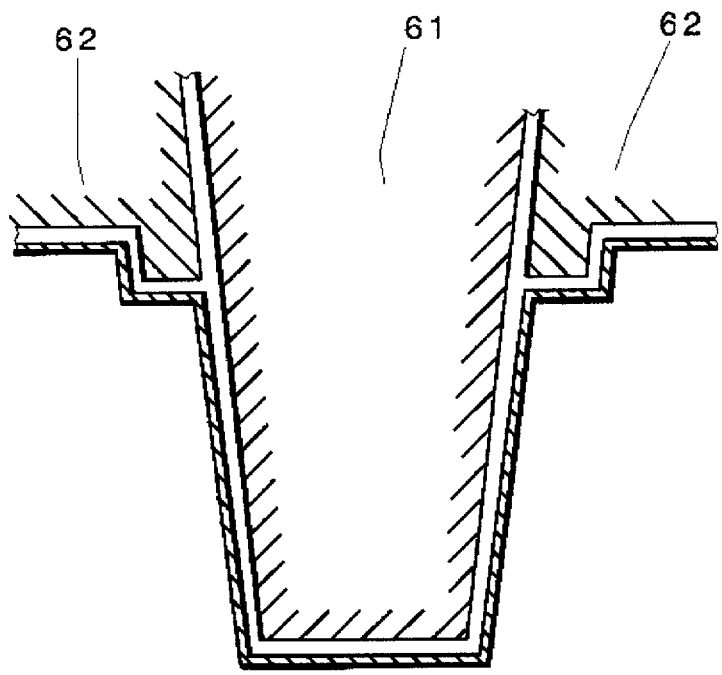
FIG. 4 is a sectional view showing a vessel form.

However, if burrs are generated on the seal surface provided by the seal member 6, they give rise to such inconvenience that liquid having been raised by capillary phenomenon along the interface between the seal member 6 and vessel and present on the seal surface may cause defective fusion between the seal member 6 and seal surface, thus resulting in leakage or evaporation of liquid. FIG. 4 is a schematic sectional view showing a vessel formation arrangement, which can prevent generation of the former inconvenience. In this case, the vessel is formed by using a die 61 for forming the vessel body and a die 62 for forming a groove along the edge of the opening of the vessel body. The width and height of the groove are both sufficiently about 0.2 mm. In this case, burrs are produced between the die 61 for the formation of the vessel body and the adjacent die 62. However, by setting the depth of the groove to be greater than the height of the burrs, it is possible to prevent defective seal due to the burrs. Further, since a plurality of dies 61 and 62 are used, a corner R is produced at a portion which is to be a corner edge. It is thus possible to eliminate the inconvenience of formation of line contact between the seal member 6 and seal surface.

Figure 5:
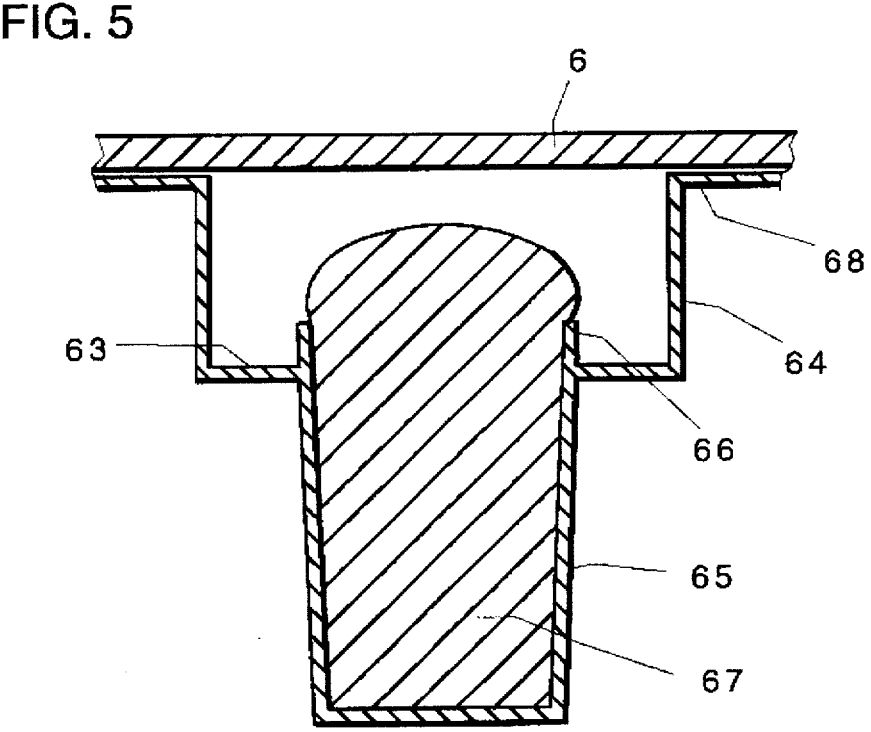
FIG. 5 is a view showing a sectional profile of the vessel.

FIG. 5 shows the sectional profile of vessel which can prevent the generation of the latter inconvenience. This vessel has a shoulder 63 formed at a predetermined position. Thus, its upper portion 64 has an increased width. In addition, an auxiliary wall 66 is formed along the most inner edges of the shoulder such that it extends along the extension of the side walls of a lower portion 65 of the vessel. The width of the shoulder 63 and the height of the auxiliary wall 66 are both sufficiently about 0.5 mm. Thus, when the lower portion 65 of the vessel is filled with liquid 67 such that the liquid is in a swelling state due to the surface tension, there is no possibility that the liquid 67 unnecessarily approaches the section of contact between the seal member 6 and seal surface 68. Also, there is no possibility that the liquid 67 rises due to the capillary phenomenon. Thus, a reliable seal can be attained with the seal member 6.

Figure 6:
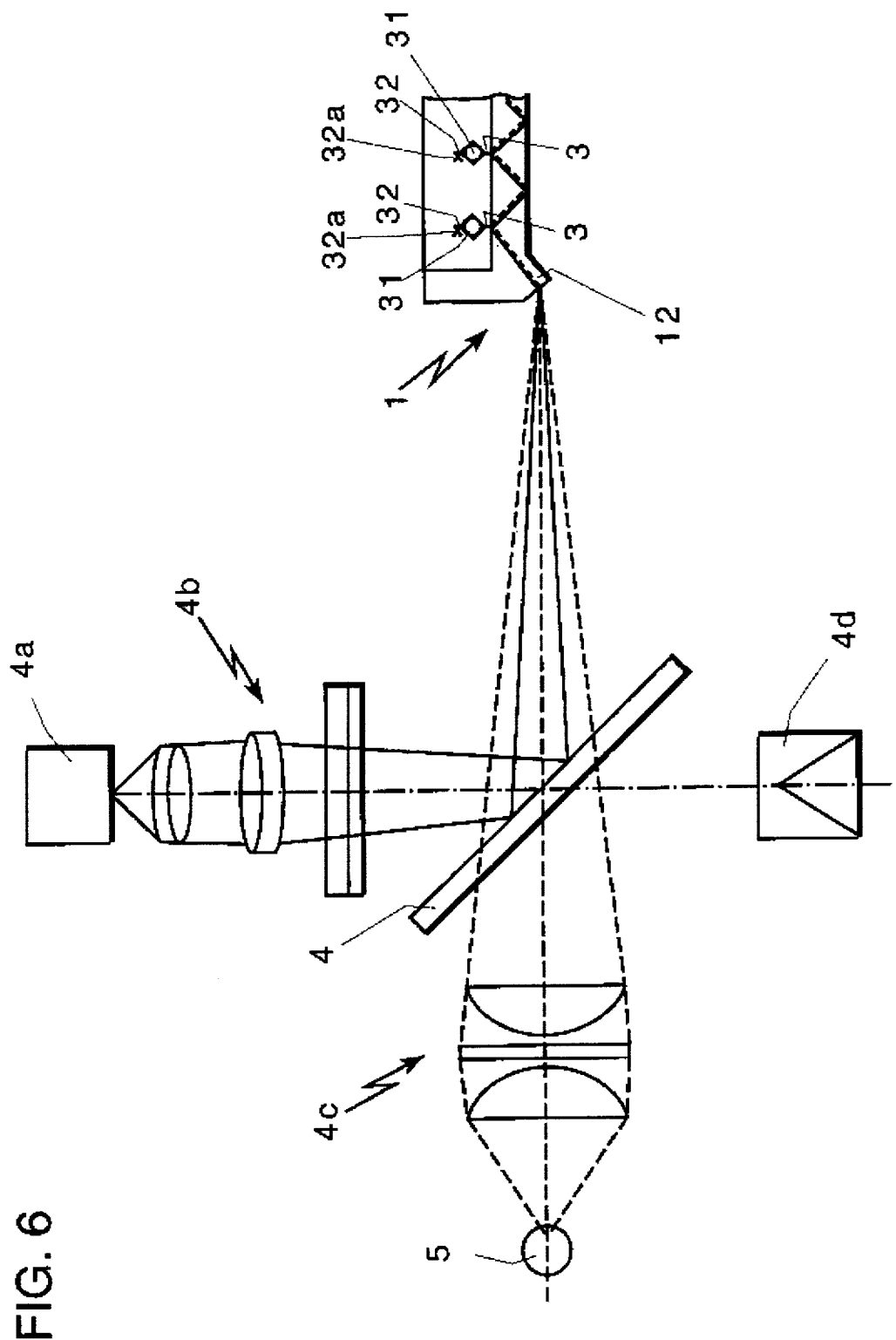
FIG. 6 is a sectional view for schematically explaining optical immunity measurement.

For carrying out immunity measurement by using the fluorescent immunity measurement apparatus, which is formed in the above way and accommodates solution, first the seal member 6 is separated, then the solution containing antigens 31 is diluted n the pre-treatment vessel 23 by taking out the diluting solution from the pre-treatment vessel 21, and then a reagent containing fluorescent label antibodies 32 is diluted in the pre-treatment vessel 22. The reagent may be diluted simultaneously with or after the dilution of the liquid under test. Then, the diluted liquid under test is poured into the reaction vessel 24. Then, the antigens 31 are caused to be received in the antibodies 3 that are attached to the optical waveguide 11, and then the liquid under test in the reaction vessel 24 is discharged. Then, as shown in FIG. 6, excitation light that is emitted from an excitation light source 4a is led via an optical system 4b and dichroic mirror 4 to the prism 12, and then the reagent which has been diluted in the pre-treatment vessel 21 is poured into the reaction vessel 24 in the casing 2. In this way, fluorescent light corresponding to the quantity of the antigens 31 can be obtained.

More specifically, with the reagent poured into the reaction vessel 24, the fluorescent label antibodies 32 in the reagent are received in the antigens 31 received in the antibodies 3. Thus, fluorescent label antibodies 32 corresponding in quantity to the quantity of the antigens in the liquid under test, are restrained in the neighborhood of the surface of the optical waveguide 11.

The excitation light as measurement light is diffracted by the prism 12 to be introduced into the optical waveguide body 11 for propagation therethrough while being totally reflected. Thus, only the label fluorescent bodies 32a of the restrained fluorescent label antibodies 32 noted above are excited by the evanescent component of the excitation light to radiate peculiar fluorescent light.

Figure 7:
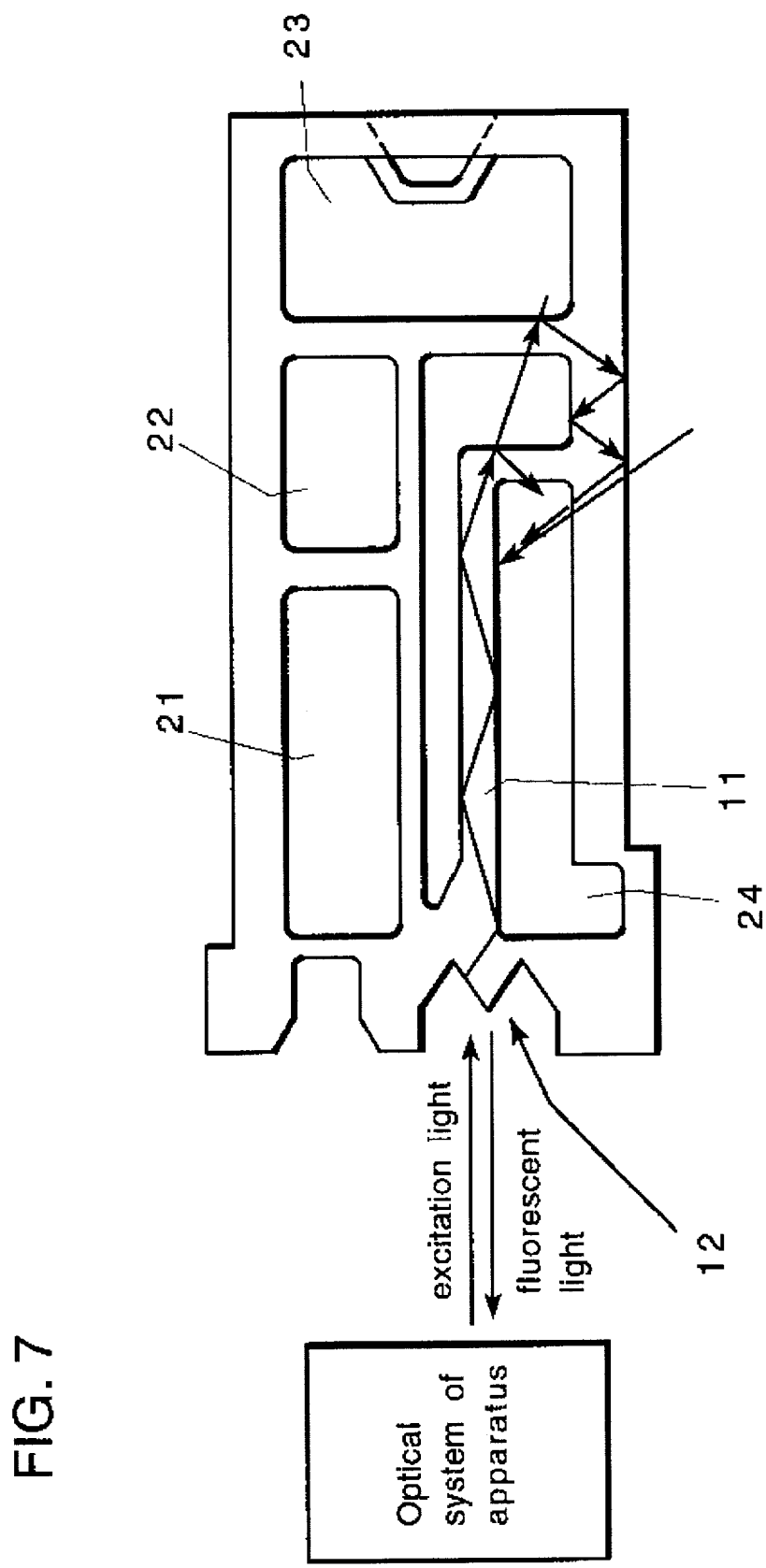
FIG. 7 is a view for explaining an inconvenience of an optical measurement apparatus without light absorber vessel.

This fluorescent light is partly propagated through the optical waveguide body 11 to be emitted from the prism 12 for reflection by the dichroic mirror 4 and optical system 4c including a filter to be led to the detector 5. In the prior art optical measurement apparatus, fluorescent light excited in the optical waveguide body 11, Raman scattering, etc. are reflected by the end surface of the optical waveguide body to be emitted from the light incidence side. In this embodiment, both the excitation light and fluorescent light that have been propagated up to a position corresponding to the light absorber vessel 25, are both absorbed by the light absorber 25a accommodated in the light absorber vessel 25. It is thus possible to reliably eliminate reflection from the light emission end of the optical waveguide body 11. In this connection, if the optical measurement apparatus without the optical absorber vessel 25 is adopted, the excitation light, for instance, is reflected to some extent at the light emission end of the optical waveguide body 11, as shown in FIG. 7. The reflected light is introduced into the reaction vessel 24 to excite the label fluorescent bodies of the floating fluorescent label antibodies, and fluorescent light emitted from the label fluorescent bodies functions as noise component. In this embodiment, however, the reflected component of the excitation light from the light emission end can be removed, as noted before, and thus the noise component can be reduced. Designated at 4d is a light-receiving element for monitoring the intensity of the excitation light.

Figure 8:
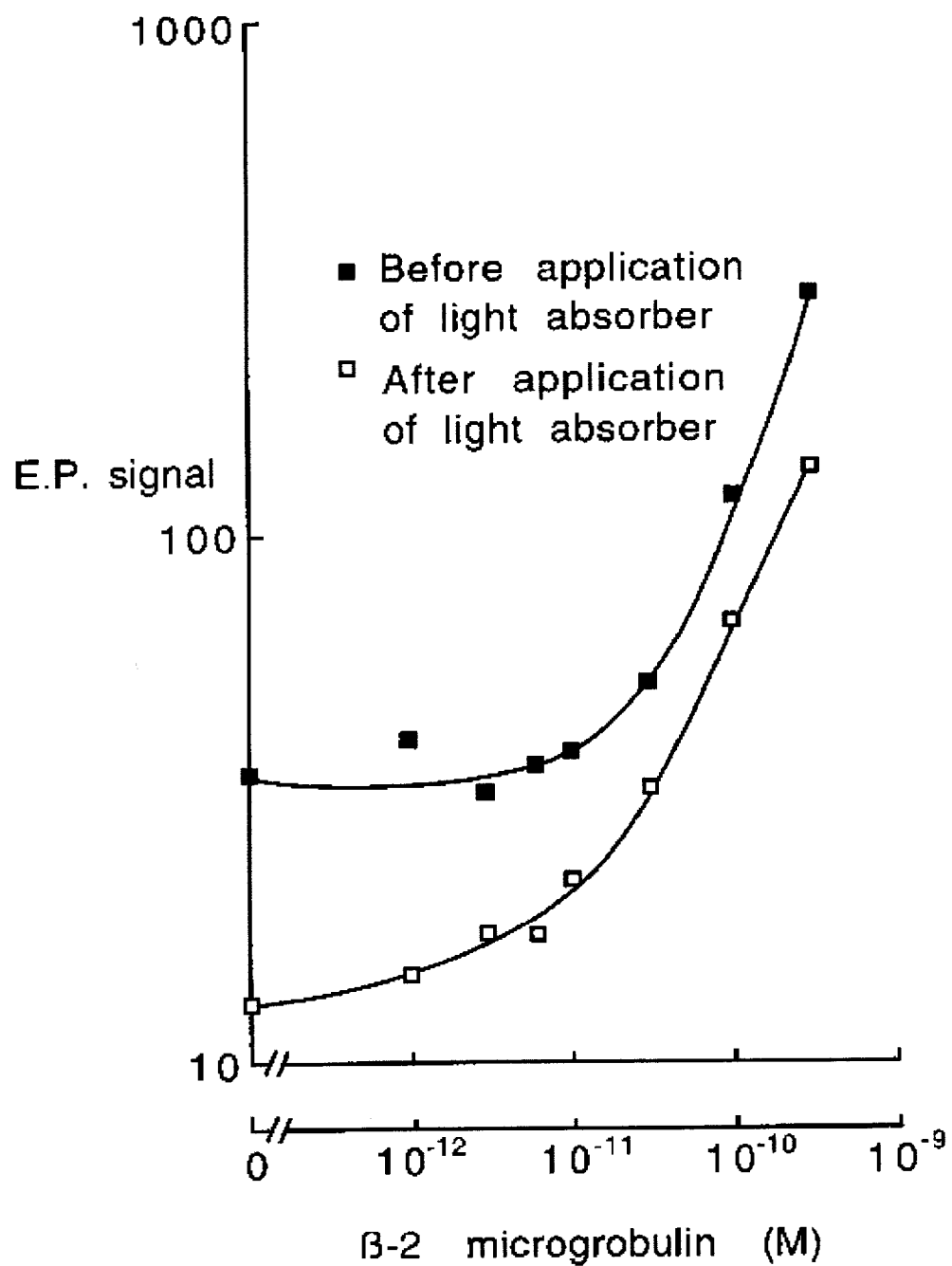
FIG. 8 is a view showing optical immunity measurement results.

Thus, the reflected component of excitation light and also the fluorescent light excited in the optical wave guide body 11, Raman scattering, etc., these being incident on the detector 5, can be extremely reduced to increase the accuracy of measurement. Further, there is a reflection component when the excitation light is incident on the prism 12. This reflection component, however, is propagated in a direction which is irrelevant to the measurement and does not function as background noise. FIG. 8 is a view showing the immunity strength corresponding to the amount of β-2 microgrobulin. It will be seen that the background noise can be greatly reduced by using the light absorber charged in the light absorber vessel 25. In FIG. 8, white squares represent the case of using light absorber, and black squares represent the case of using no light absorber. As is obvious from FIG. 8, without use of any light absorber the sensitivity of measurement is $1\times10^{-11}$M, whereas by using the light absorber it is increased up to $6\times10^{-12}$M. Further, in the case of setting the wavelength of the excitation light to 495 nm and using FITC as the fluorescent pigment, the S/N ratio (i.e., the ratio between the real immunity signal value and an off-set stray light signal value) is 0.136, which is 1.94 times the value in the case of using no light absorber.

Further, the optical waveguide body 11 is formed to be substantially vertical. Thus, when proteins and like disturbance matter in the liquid under test settle and deposited, the surface, to which antibodies are attached, is hardly covered by the deposited matter. It is thus possible to introduce measurement light of a sufficient intensity into the optical waveguide body 11. Further, since the fluorescent light immunity measurement apparatus is formed as a one-piece molding, there is substantially no fluctuation of the position, at which the prism 12 is formed. Thus, fine adjustment of the prism position for the fluorescent light immunity measurement is unnecessary.

Further, since the liquid under test can be discharged substantially completely before distributing the reagent containing fluorescent label antibodies, it is possible to obtain measurement results with very less fluctuations compared to the case of fluorescent light immunity measurement using the apparatus shown in FIG. 24, as shown in Table 1 below. In the table, n represents the number of times of repetition, β2 m represents β2 microgloburin, and CRP represents C-reactive protein.

TABLE 1

Figure 24:
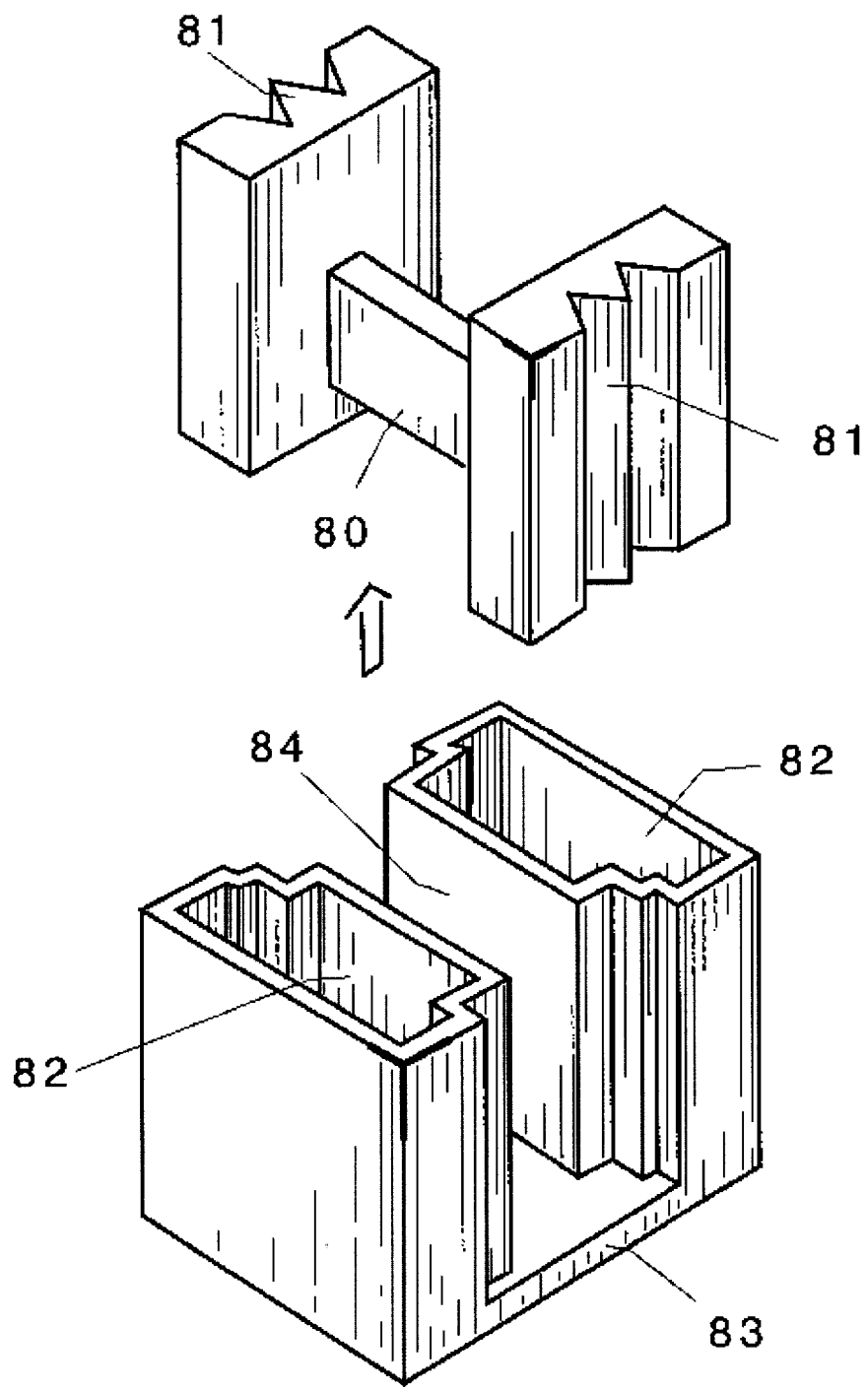
FIG. 24 is an exploded perspective view showing a prior art proposed improvement over optical measurement apparatus.
Figure 25:
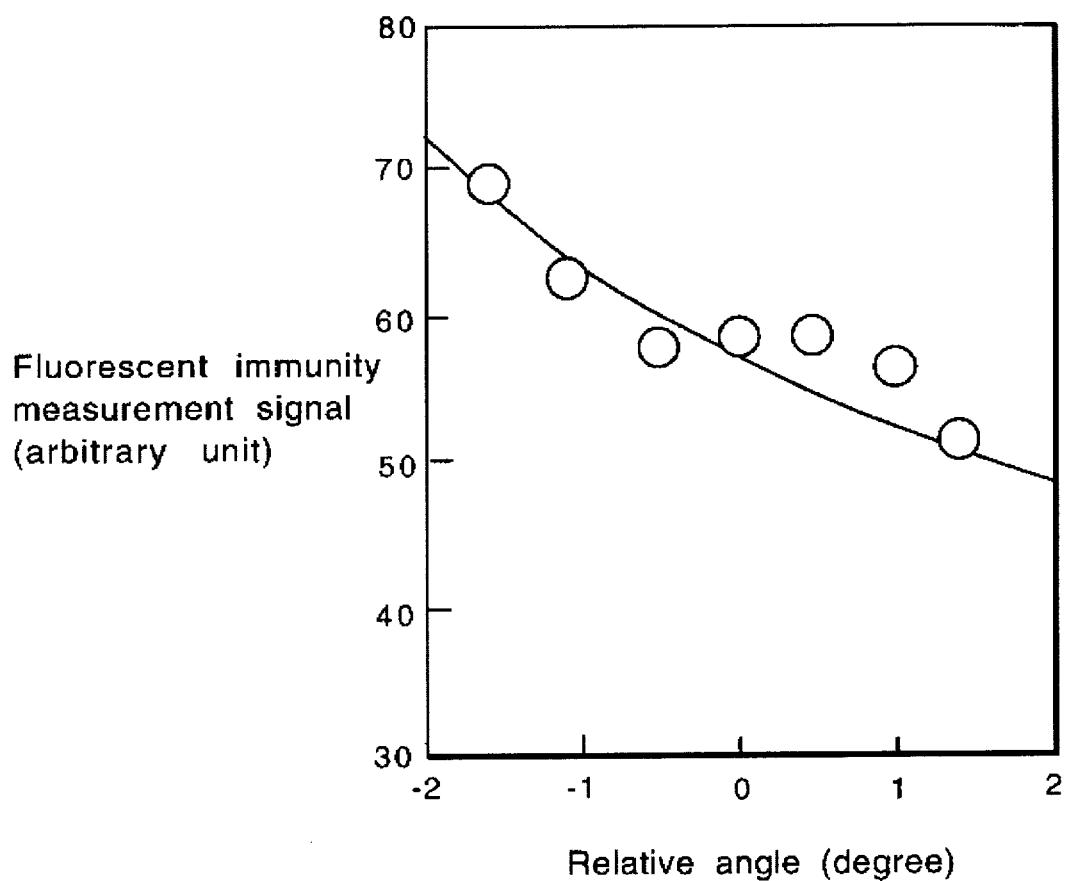
FIG. 25 is a graph showing fluctuating fluorescent immunity measurement signal obtained with the optical measurement apparatus shown in FIG. 24.

|  | Optical measurement apparatus in FIG. 24 | Optical measurement apparatus in according to the invention |
|---|---|---|
| Residual value (n = 5) | 52.1 μl | 20.9 μl |
| CV vlaue | 44.9% | 10.5% |
| Fluorescent light immunity measurement signal (n = 6) | 114.0 | 147.5 |
| CV value | 12% (high concentration β 2 m) | 1.6% (high concentration CRP) |

Further, since at least part of the side walls of the reaction vessel 24 is transparent, the position of distribution of the liquid under test or the like could be confirmed with the eyes, and thus fluctuations of the fluorescent light immunity measurement due to fluctuations of the distribution position could be greatly suppressed. Table 2 below shows fluorescent light immunity measurement signals and fluctuations thereof when the position of the distribution of the liquid under test was set to a left and a right position, indicating that the extent of stirring varies depending on the position of the distribution.

TABLE 2

|  | Position of distribution of liquid under test | |
|---|---|---|
|  | Left | Right |
| Fluorescent light immunity measurement signal (n = 6) | 103.1 | 117.6 |
| CV value | 4.0% | 2.9% |

In this embodiment, a nozzle for the operations of diluting the liquid under test and reagent and pouring the diluted solution and reagent into the reaction vessel 24, is moved along an orbit as shown by arrow A in FIG. 1. As is seen, the orbit is an arcuate simple one, and thus the control of the nozzle for the above operations can be simplified. Further, it is possible to off-set the reaction vessel 24 to reduce the thermal resistance so as to reduce the taken for the reaction solution to be elevated in temperature from the preservation temperature (for instance 4° C.) to the reaction temperature (for instance 37° C.). However, it is possible to use the sole pre-treatment vessel 23 for diluting the liquid under test containing the antigens 31 and pouring the fluorescent label antibodies 32 for mixing. In this case, there is no need of using the pre-treatment vessel 22.

In this embodiment, the inner surfaces of the light absorber vessel 25 is suitably polished to be like a mirror surface. By so doing, it is possible to greatly suppress random reflection of the excitation light due to otherwise present irregularities of the inner surfaces of the light absorber vessel 25. Thus, the efficiency of absorption of the excitation light by the light absorber 25a can be increased to obtain satisfactory reproducibility in a low concentration range. As a specific example, the coarseness of two molding samples (which are shaped at a time, for instance) was measured in a state, in which the inner surfaces of the light absorber vessel 25 had been polished by #2,000 polishing, and also in a state, in which the inner surfaces were had been further polished by #20,000 polishing. Further, the reproducibility was evaluated by measuring the CV values in the high and low concentration ranges.

Table 3 shows the coarseness of the moldings, and Table 4 shows the results of the reproducibility evaluation. In the tables, Ra represents the projection (μm) from an average line, Rz (DIN) represents the mean coarseness (μm) for 10 points, and the reproducibility evaluation value represents the fluctuations (CV values) from the average value. "Before polishing" means the state after the sole #2,000 polishing, and "After polishing" means the state after the #20,000 polishing.

TABLE 3

|  | Sample 1 | | Sample 2 | |
| --- | --- | --- | --- | --- |
|  | Before polishing | After Polishing | Before Polishing | After Polishing |
| Ra | 0.16 | 0.08 | 0.18 | 0.08 |
| Rz (DIN) | 1.16 | 0.48 | 1.22 | 0.58 |

TABLE 4

|  | Sample 1 | | Sample 2 | |
| --- | --- | --- | --- | --- |
|  | Before Polishing | After Polishing | Before Polishing | After Polishing |
| High concentration range | 4% | 10% | 7% | 7% |
| Low concentration range | 10% | 5% | 25% | 7% |

As is clear from the these measurement results, by providing the polishing the surface roughness of the inner surfaces of the light absorber vessel 25 is extremely improved (i.e., the surfaces are made extremely flat), thus extremely improving the reproducibility of measurement in the low concentration range. In the high concentration range, however, the reproducibility of measurement is not changed or rather reduced. This is thought to be due to the fact that influence of the apparatus is liable in the low concentration range while influence of the fluctuations of the immunity reaction itself is liable in the high concentration range.

Embodiment 2

Figure 9:
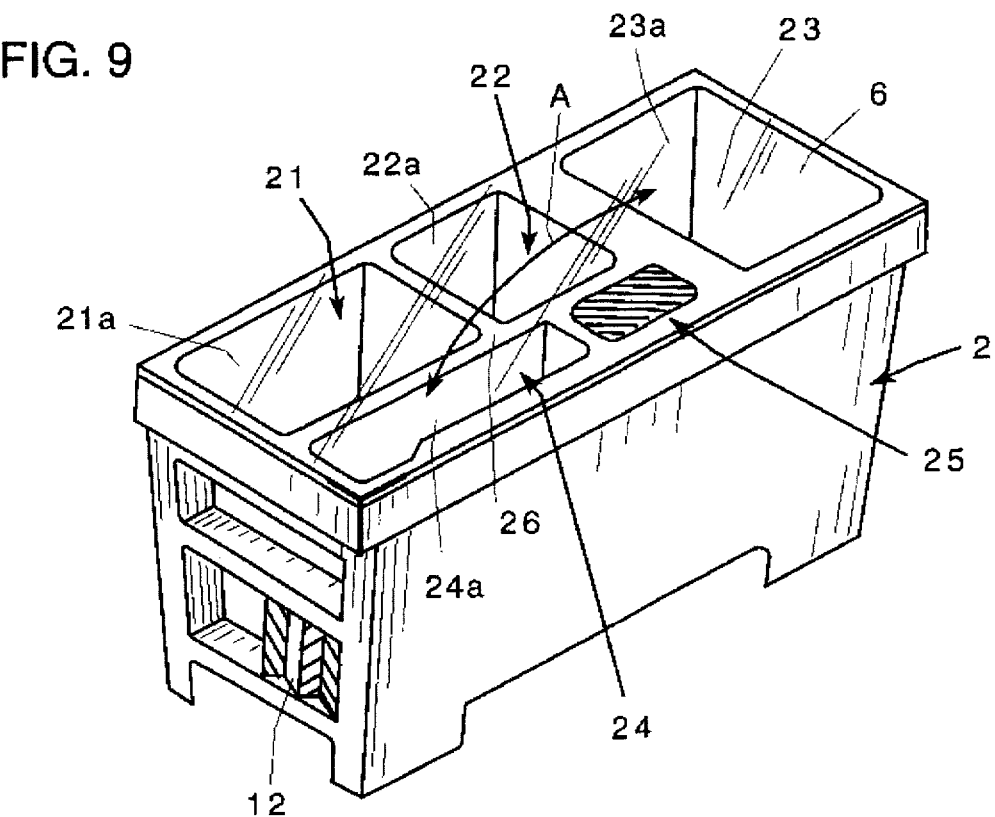
FIG. 9 is a schematic perspective view showing a different embodiment of the optical immunity measurement apparatus according to the invention.
Figure 10:
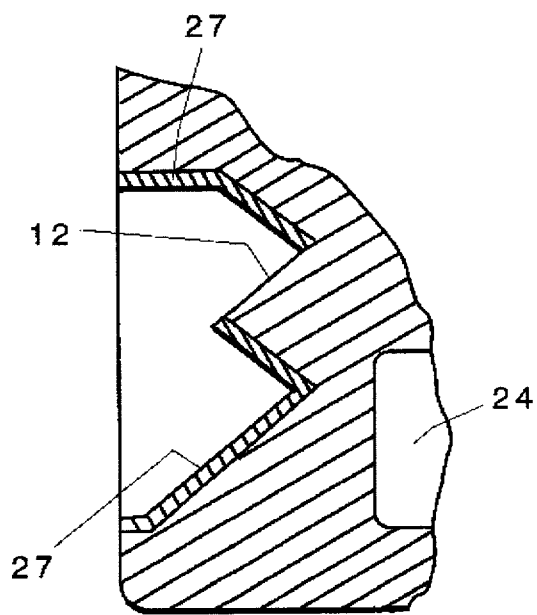
FIG. 10 is a fragmentary sectional view.

FIG. 9 is a schematic perspective view showing a different embodiment of the optical measurement apparatus according to the invention. FIG. 10 is a fragmentary sectional view. This embodiment is different from the preceding optical measurement apparatus shown in FIG. 1 only in that light blocking members 27 are provided in predetermined areas except for and adjacent to an excitation light introduction area (i.e., measurement light emission area) on the side of the prism 12. Again in FIG. 9, the internal structure of the apparatus is not shown.

The light blocking member 27 may use both light absorber and light reflector. The light blocking member 27 made of a light absorber may be coated with a black paint. Instead, it is possible to form an integral black synthetic resin layer on one side of a transparent synthetic resin. The light blocking member 27 made of a light reflector may be formed by applying a metal foil or the like.

Figure 11:
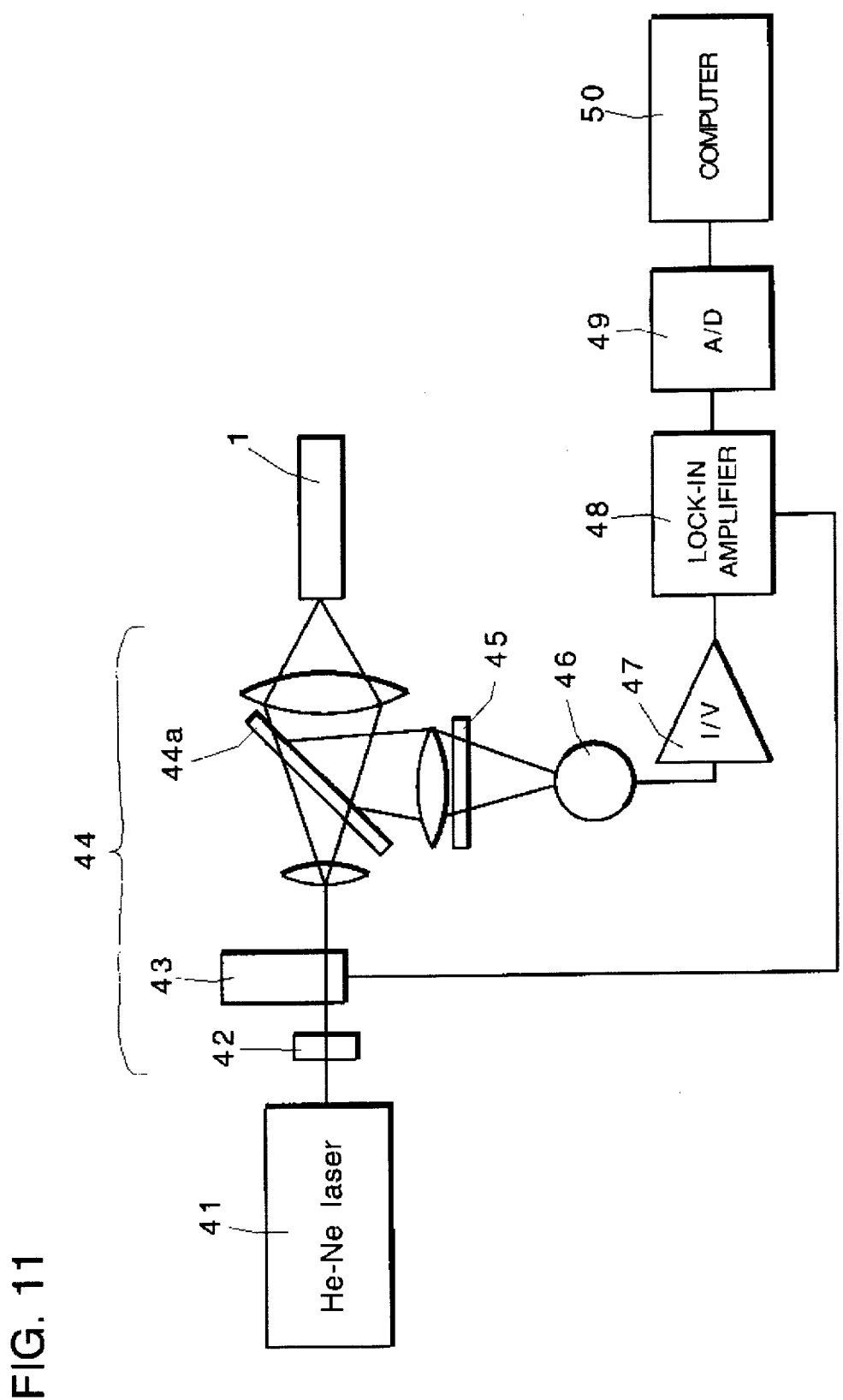
FIG. 11 is a schematic view showing a measurement apparatus for carrying out optical measurement with the optical measurement apparatus shown in FIG. 9.

FIG. 11 schematically shows the overall structure of a measurement system for making optical measurement with the optical measurement apparatus shown in FIG. 9. Light emitted from a He—Ne laser 41 as an excitation light source is led via a ND (neutral density) filter 42, a light chopper 43 and a lens system 44 including a dichromic mirror 44a to the excitation light introduction area of the prism 12, and measurement light emitted from the excitation light introduction area of the prism 12 is led by the dichroic mirror 44 in the lens system 44 in a direction different from the excitation light and then led via a sharp cut filter 45 to a photoelectron multiplier 46. The photoelectron multiplier 46 provides an output current, which is amplified by an I/V converter 47, then detected by a lock-in amplifier 48 and then amplified by an A/D converter 49 before being fed to a computer 50 for various kinds of signal processing. To the lock-in amplifier 48 is supplied a synchronous signal corresponding to the operation of the light chopper 43.

The optical measurement apparatus having the above structure operates as follows.

Light from the He—Ne laser 41 is modulated in the light chopper 43 and then led to the optical measurement apparatus. In the optical measurement apparatus, the excitation light is introduced from the sole excitation light introduction area of the prism 12. As the introduced excitation light is propagated through the optical waveguide body 11, its evanescent wave component excites the fluorescent label antibodies 32 which are restrained in the neighborhood of the surface of the optical waveguide body 11, thus generating fluorescent light having a predetermined wavelength.

The fluorescent light generated from the fluorescent label antibodies 32, is propagated through the optical waveguide body 11 to be emitted as measurement light from the sole excitation light introduction area of the prism 12 and led to the photoelectron multiplier 46. At this the, light due to light generation, scattering, etc. in other portions than the neighborhood of the surface of the optical waveguide body 11, is blocked by the light blocking member 27. Thus, it is reliably prevented from being led as noise light component with respect to the measurement light to the photoelectron multiplier 46.

Thus, it is possible to extremely increase the S/N ratio of the output current (i.e., measurement signal) from the photoelectron multiplier 46 and hence extremely increase the sensitivity of the optical measurement using the optical measurement apparatus.

Figure 12:
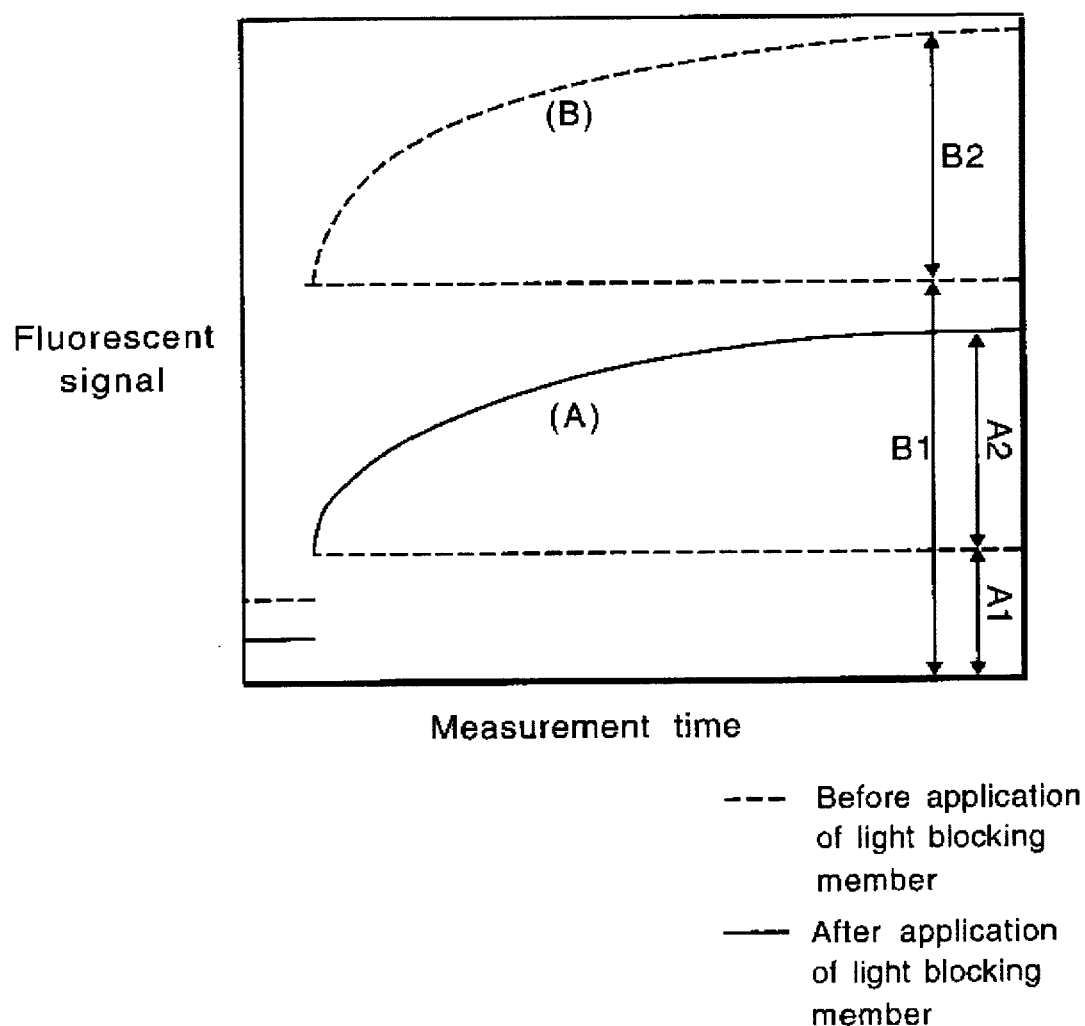
FIG. 12 is a graph showing a fluorescent light signal obtained with the embodiment of the optical measurement apparatus shown in FIG. 9 and a fluorescent light signal obtained with an optical measurement apparatus without any light blocking member, these signals being plotted against time.

FIG. 12 shows a fluorescent signal obtained with the embodiment of the optical measurement apparatus (refer to A in FIG. 12) and a fluorescent signal obtained with an optical measurement apparatus without the light blocking member 27 (refer to B in FIG. 12), these fluorescent signals being plotted against time. It will be seen that with this embodiment the noise level can be greatly reduced.

In this specific example, as the light blocking member 27 is used one, which is obtained by coating a black paint for acrylic acid resin, and the illustrated fluorescent signals are obtained in the measurement of 1 ng/ml of β-2 microglobulin. In FIG. 12, labelled A1 and B1 are noise levels, and labelled A2 and B2 are measurement signal levels based on β-2 microglobulin. Of these fluorescent signals, the S/N ratio at a point of substantial saturation of the measurement signal is 1.3 and 0.6, respectively. Thus, it will be seen that in this embodiment the S/N ratio is extremely improved.

Figure 13:
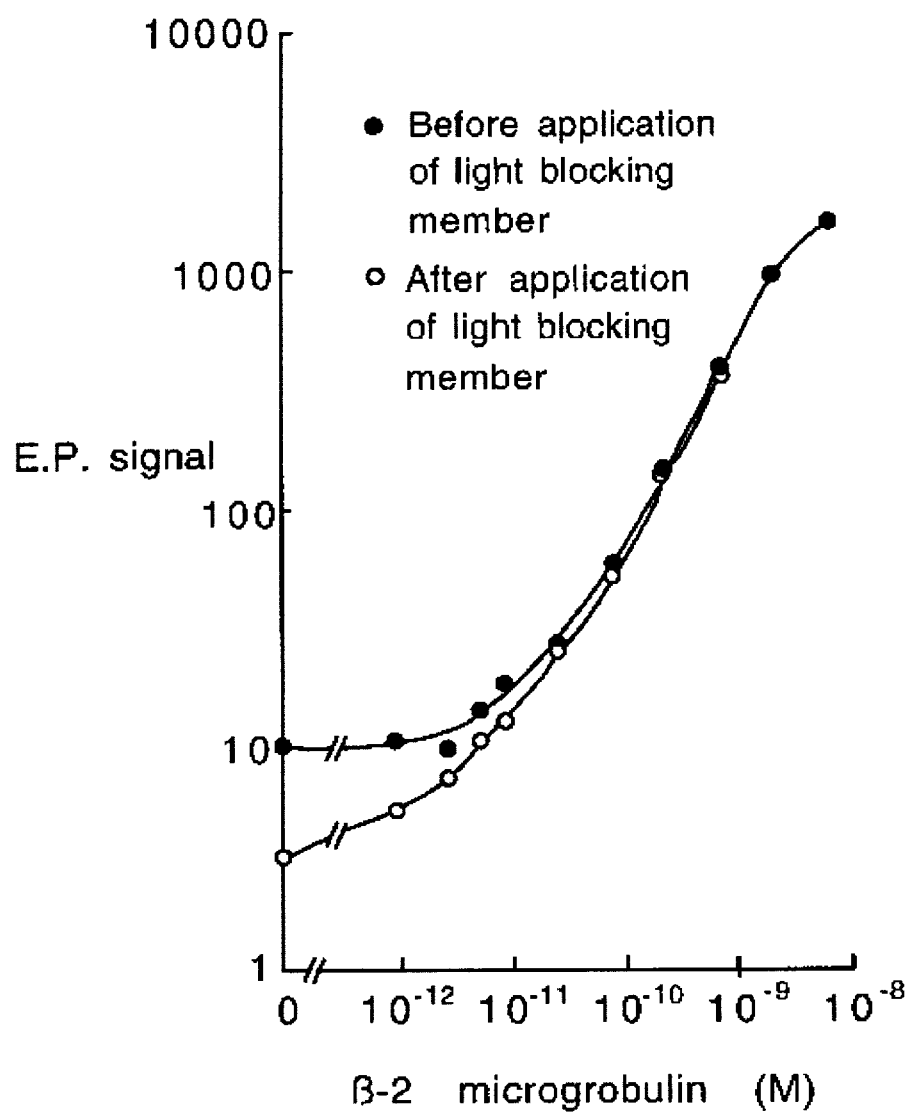
FIG. 13 is a graph showing a calibration curve obtained with the embodiment of the optical measurement apparatus shown in FIG. 9 and that obtained with an optical measurement apparatus without light blocking member.

FIG. 13 is a view showing a calibration curve (see white circles in FIG. 13) obtained by using the embodiment of the optical measurement apparatus and that (see black circles in FIG. 13) obtained by using an optical measurement apparatus without the light blocking member 27. In the latter the sensitivity of measurement is $1 \times 10^{-11}$M, while it is $1 \times 10^{-12}$M in the latter. It will be seen that the sensitivity of measurement can be extremely increased.

While in this embodiment the light absorber 25a is not used, it is possible to use the light absorber 25a. In this case, it is possible to improve the S/N ratio and the sensitivity of measurement more pronouncedly.

Embodiment 3

Figure 14:
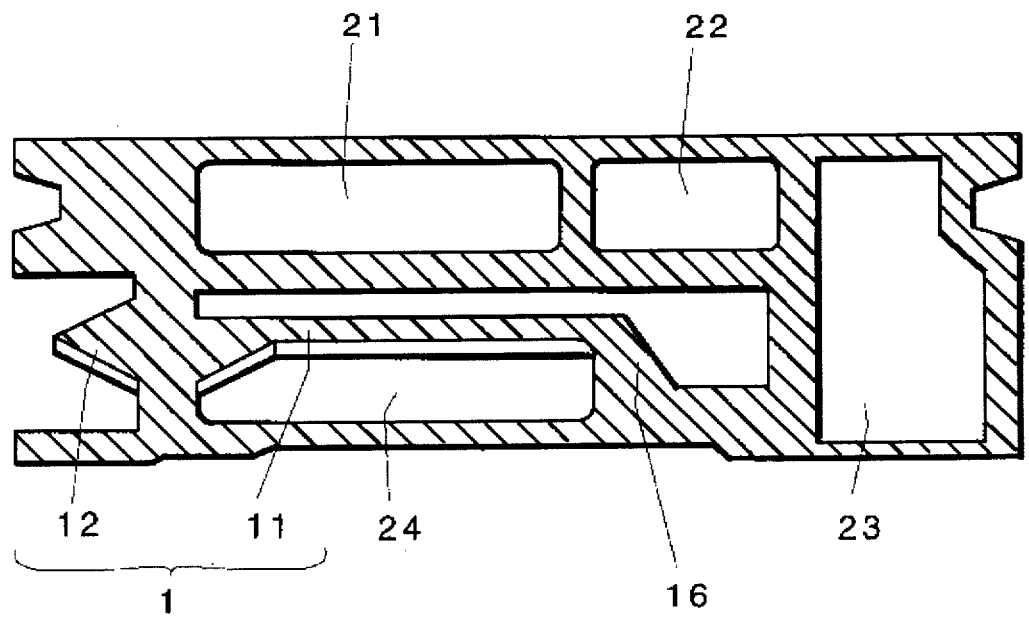
FIG. 14 is a sectional view showing a further embodiment of the optical measurement apparatus according to the invention.

FIG. 14 is a sectional view showing a further embodiment of the optical measurement apparatus according to the invention. This embodiment is different from the embodiment shown in FIG. 1 in float the light absorber vessel 25 is omitted and that the trailing end of the optical waveguide body 11 is formed with an integral total reflection prism 16 such that excitation light having been propagated through the optical waveguide body 11 is emitted in a direction at a predetermined angle (for instance 90°) to the optical axis of the optical wave, guide body 11.

Figure 15:
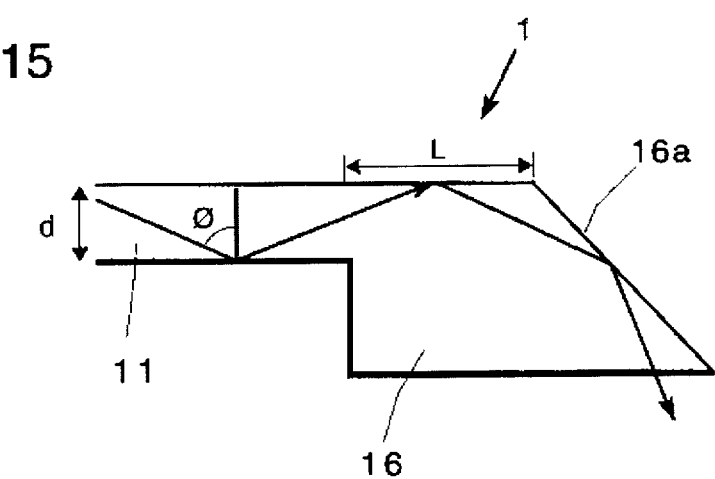
FIG. 15 is a fragmentary enlarged-scale view showing the same embodiment.

The total reflection prism 16 has an area, which constitutes an extension of one surface of the optical waveguide body 11 and has a length L, an area, which constitutes a surface extending substantially perpendicularly from a surface opposed to the afore-mentioned one surface of the optical waveguide body 11, and a total reflection area 16a (and is at an angle of 35°, for instance, with respect to the above length L area), which is continuous to the above area with the length L (see FIG. 15). Denoting the thickness of the optical waveguide body 11 by d and the excitation light propagation angle by θ, the length L noted above may be set to satisfy $$L \geq d/\tan \theta$$

If this is done so, the excitation light propagating through the optical waveguide body 11 can be wholly totally reflected by the total reflection surface 16a to be emitted in the direction noted above.

Thus, it is possible to dispose the pre-treatment vessel 23, such as a reagent vessel, at a position oil the extension of the optical waveguide body 11 to reliably preclude the influence of the excitation light on the pre-treatment vessel 23 disposed in this way. It is thus possible to increase the degree of freedom of the pre-treatment vessel disposition and also easily increase the number of pre-treatment vessels or the like that are to be disposed. Further, in the case of this embodiment, cost reduction compared to the embodiment shown in FIG. 1 is attainable because the light absorber 25a is unnecessary.

Embodiment 4

Figure 16:
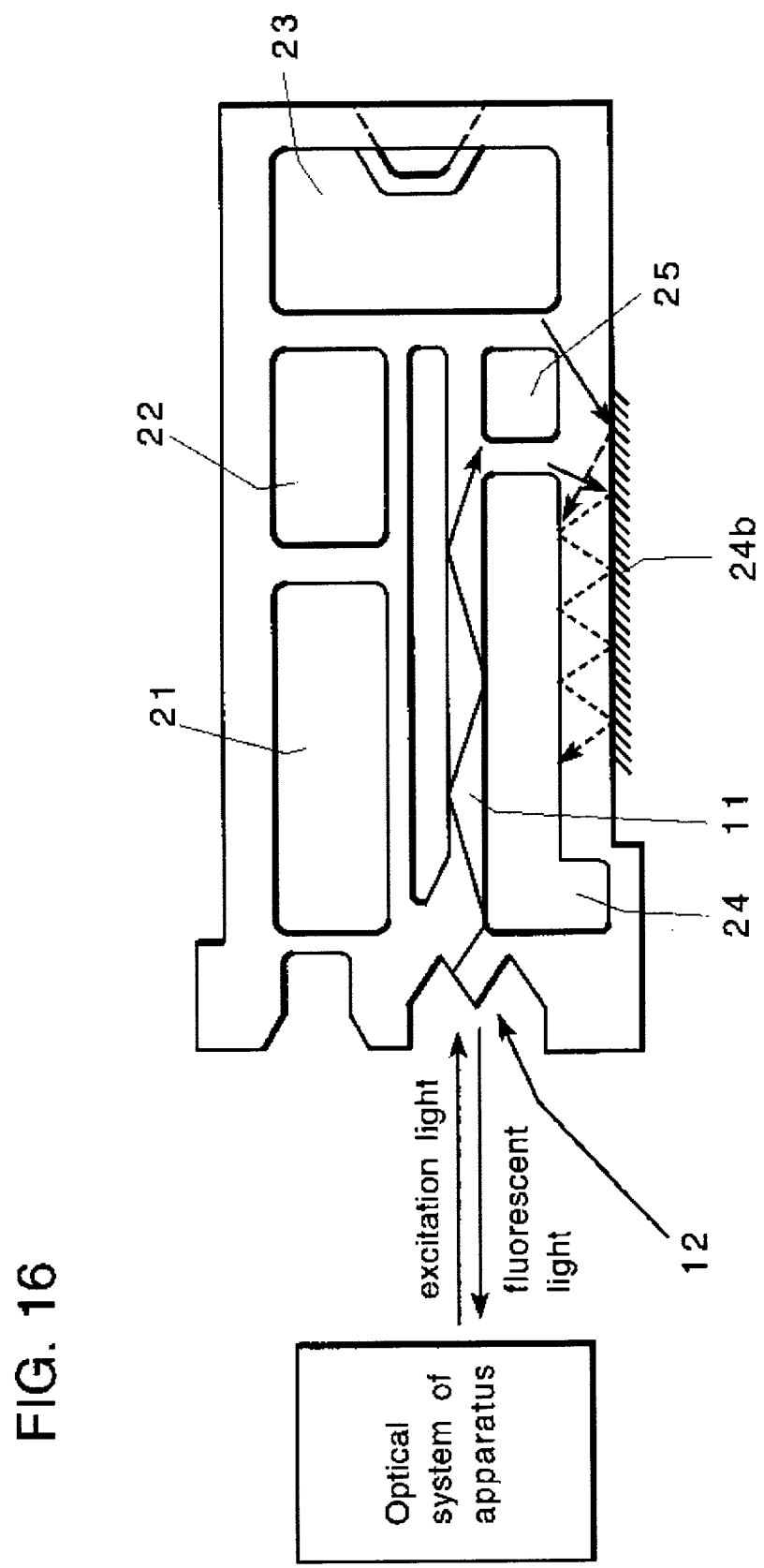
FIG. 16 is a sectional view showing a further embodiment of the optical measurement apparatus according to the invention.

FIG. 16 is a sectional view showing a further embodiment of the optical measurement apparatus according to the invention. This embodiment is different from the embodiment shown in FIG. 1 in that the light absorber vessel 25 is omitted and that substantially the entire outer surface of the wall of the reaction vessel 24 that opposes the optical waveguide body 11 is coated with black paint 24b. The black paint 24b that may be used is any paint having no influence on the solution to be poured into the reaction vessel 24. In the figure, no shading is used in order to clearly show the path of propagation of the excitation light. The dashed line shows an example of scattered component of the excitation light in the case where the black paint 24b is not coated.

The excitation light laving been propagated through the optical waveguide body 11 is scattered or reflected, so that it is partly led to the side wall opposing the optical waveguide body 11. However, the excitation light that has been led to the side wall with black paint is absorbed by the black paint 24b and sufficiently attenuated. Thus, it is possible to extremely reduce the intensity of light that is led from the side wall noted above into the reaction vessel 24. Consequently, it is possible to extremely reduce the noise component due to excitation light on the basis of the above path. As a specific example, with the excitation light wavelength set to 495 nm while using FITC as the label fluorescent material, the S/N ratio (i.e., the ratio of the real immunity signal value to the stray light signal value as an off-set) was 0.146, which is 2.09 times the value in the case where the black paint is not used. Suitably, instead of coating the outer surface of the side wall with the black paint 24b, the inner surface of the side wall is coated with black paint.

Of course, it is suitable to use the light absorber vessel 25 as well, as shown by phantom line in FIG. 16. In this case, it is possible to further increase the noise component reduction effect.

Embodiment 5

Figure 17:
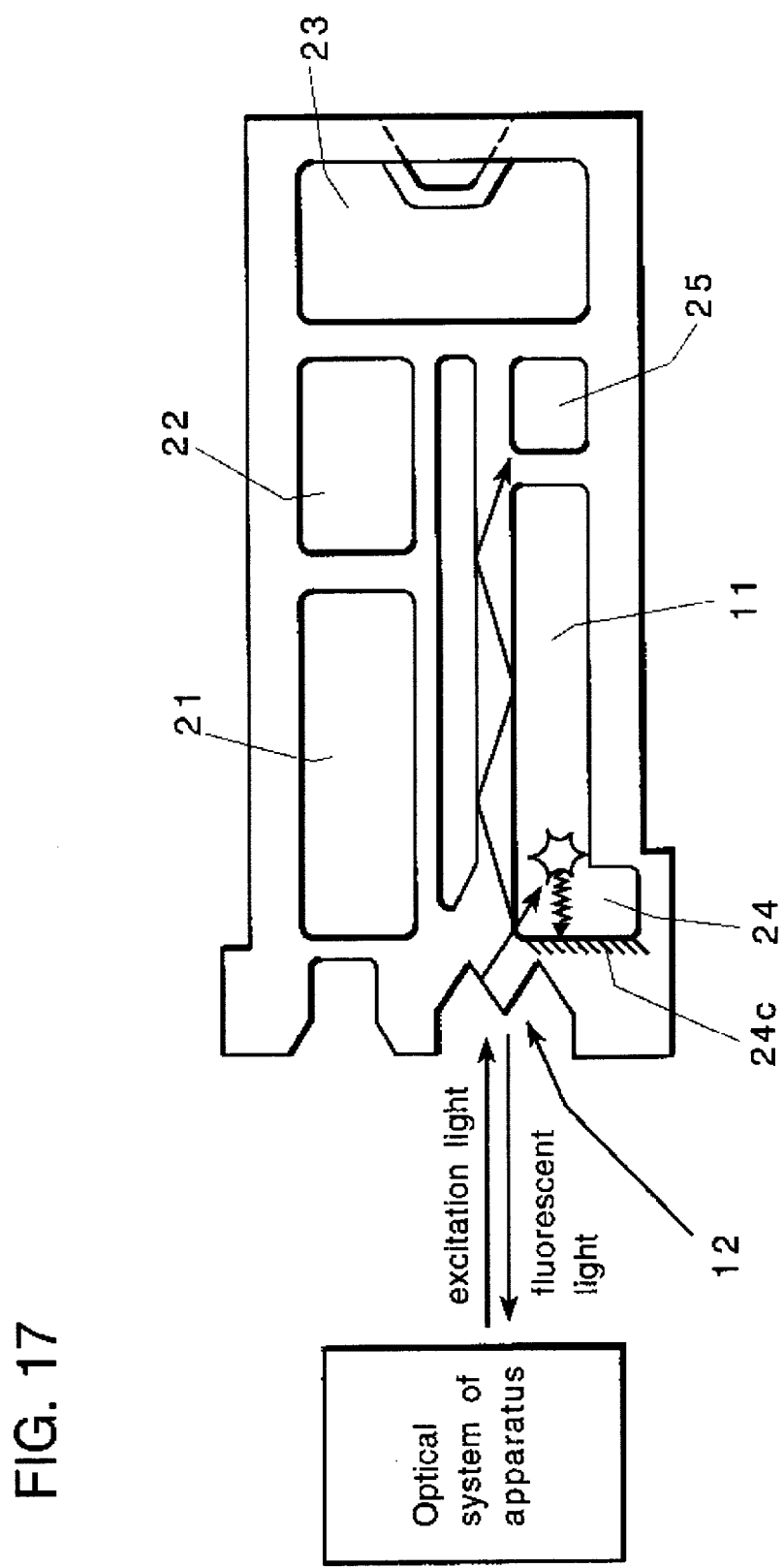
FIG. 17 is a sectional view showing a still further embodiment of the optical measurement apparatus according to the invention.

FIG. 17 is a sectional view showing a further embodiment of the optical measurement apparatus according to the invention. This embodiment is different from the embodiment shown in FIG. 16 only in that, instead of coating the black paint 24b on substantially the entire surface of the side wall of the reaction vessel 24 opposing the optical waveguide body 11, the inner surface of the wall, which extends perpendicularly to the optical waveguide body 11 and is located on the side of the prism 12, is coated with black paint 24c. In the figure, no shading is used in order to clearly show the path of propagation of the excitation light.

Thus, like Embodiment 2 of the optical measurement apparatus, it is possible to reduce the noise level. In Embodiment 2 of the optical measurement apparatus, the noise component that is radiated from the reaction vessel 24 and led to the prism 12, can not be blocked. In contrast, in this embodiment the noise component radiated from the reaction vessel 24 can be reliably prevented from being led to the prism 12. It is thus possible to attain higher noise level reduction effects. As a specific example, with the excitation light wavelength set to 495 nm while using FITC as the label fluorescent material, the S/N ratio (i.e., the ratio of the real immunity signal value to the stray light signal value as an off-set), was 0.273, which is 3.90 times the value in the case of using no black paint.

This embodiment will further be described.

The excitation light having been led through the prism 12 into the optical waveguide body 11, is propagated through the same while being totally reflected. However, since the surfaces of the optical waveguide body 11 are not perfectly flat surfaces, the excitation light partly intrudes into the reaction vessel 24. In addition, the angle of incidence of the excitation light fluctuates to a certain extent, and therefore the excitation light partly intrudes into the reaction vessel 24 due to its first reflection by the prism 12. Such intruding light excites the label fluorescent material floating in the reaction vessel 24, thus causing generation of fluorescent light from the floating label fluorescent material. In this embodiment, the black paint 24c prevents the fluorescent light generated by the floating label fluorescent material from being emitted toward the prism 12. It is thus possible to attain higher noise level reduction effects as noted above.

Embodiment 6

Figure 18:
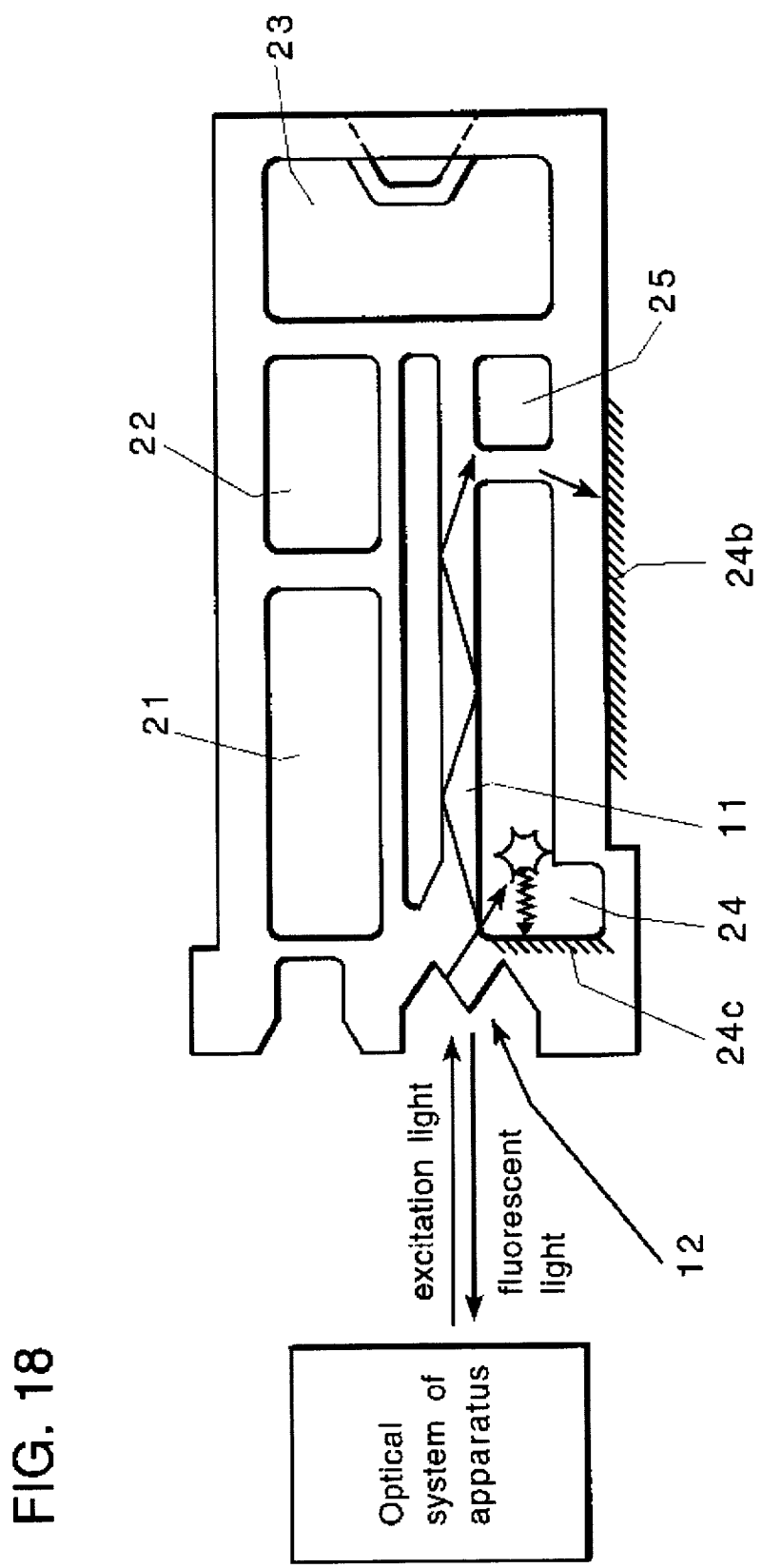
FIG. 18 is a sectional view showing yet further embodiment of the optical measurement apparatus according to the invention.

FIG. 18 is a sectional view showing a further embodiment of the optical measurement apparatus according to the invention. This embodiment is different from the embodiment shown in FIG. 16 only in that the inner surface of the side wall of the reaction vessel 24 that extends perpendicularly to the optical waveguide body 11 and is located on the side of the prism 12 is also coated with the black paint 24c. In the figure, no shading is used to clearly show the path of propagation of the excitation light.

Thus, in this embodiment the effects obtainable in Embodiments 4 and 5 can be attained in combination to attain yet higher noise level reduction effects.

Embodiment 7

Figure 19:
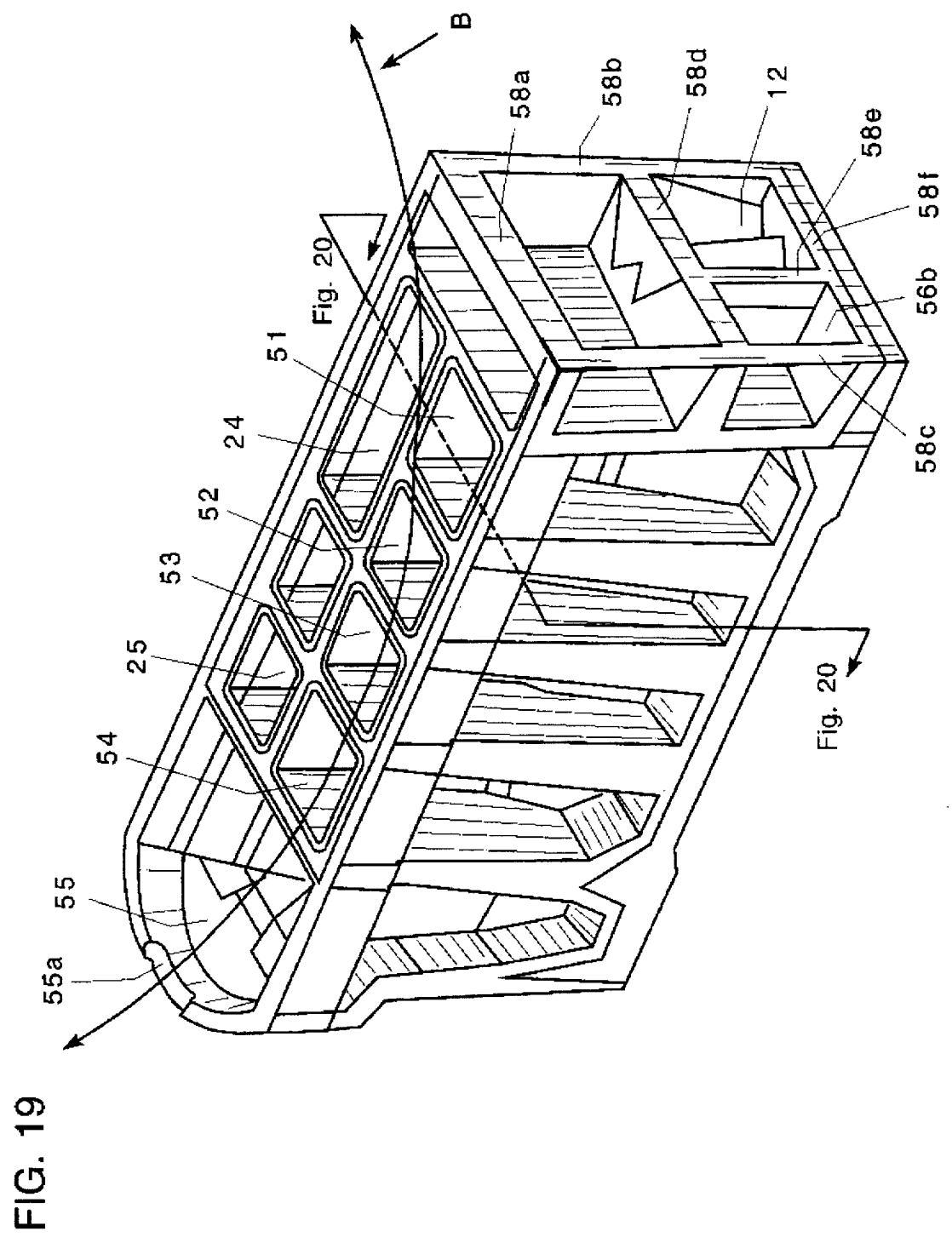
FIG. 19 is a perspective view showing a further embodiment of the optical measurement apparatus according to the invention.
Figure 20:
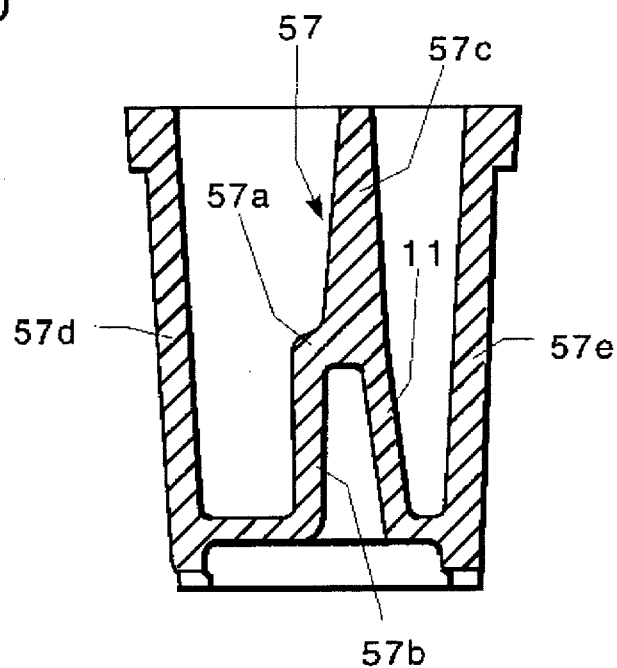
FIG. 20 is a sectional view taken along line XX—XX in FIG. 19.
Figure 21:
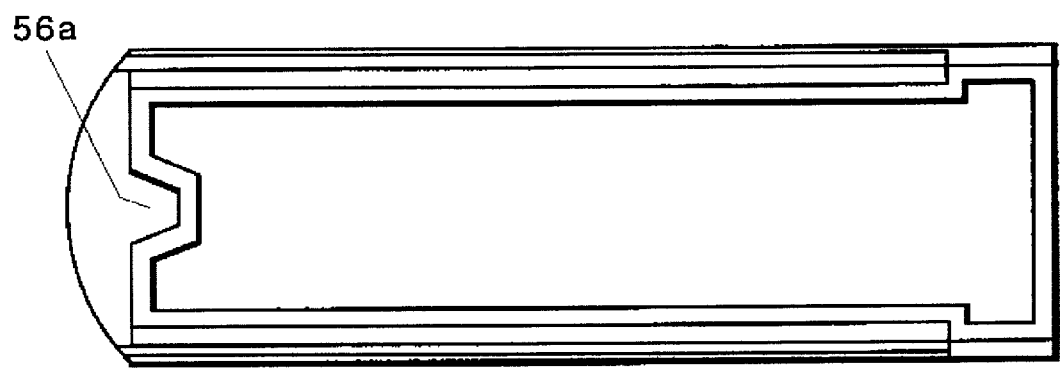
FIG. 21 is a bottom showing the optical measurement apparatus shown in FIG. 19.

FIG. 19 is a perspective view showing a further embodiment of the optical measurement apparatus according to the invention. FIG. 20 is a sectional view taken along line XX—XX in FIG. 19, and FIG. 21 is a bottom view of the embodiment. The optical measurement apparatus is made of material having transparency in its entirety. This optical measurement apparatus is different from the embodiment shown in FIG. 1 in that, in lieu of the pre-treatment vessels 21 and 22, a diluting solution vessel 51, a stirring vessel 52, a multi-function vessel 53 and a label solution vessel 54 are disposed in the mentioned order such that the diluting solution, stirring and multi-function vessels 51 to 53 regularly face the reaction vessel 24 and that the label solution vessel 54 regularly faces the light absorber vessel 25 and also that a detection vessel 55 is provided in lieu of the pre-treatment vessel 23.

The embodiment will further be described.

The diluting solution vessel 51 is for accommodating a solution (diluting solution) for diluting the liquid under test. The stirring vessel 52 is for attaining the stirring of the liquid under test and the diluting solution both poured into it. To this end, a nozzle (not shown) is used to carry out the withdrawal and discharge of the blend solution repeatedly a necessary number of times. The multi-function vessel 53 is used for accommodating a reagent for increasing dilution factor or increasing the sensitivity of the optical measurement. More specifically, for increasing the dilution factor, using a nozzle (not shown) the diluted liquid under test in the stirring vessel 52 and the diluting solution are poured, and the blend solution is withdrawn and discharged repeatedly for a necessary number of times. For the latter purpose, a solution containing biotin label antibodies 73 labelled by biotin 73a is poured in advance. The label solution vessel 54 is for accommodating a solution containing fluorescent label antibodies 32 labelled by label fluorescent material 32a or fluorescent label avidin 72 labelled by label fluorescent material 72a. This vessel regularly faces none of the side walls of the reaction vessel 24. Thus, when the label fluorescent material is excited by excitation light propagated through the optical waveguide body 11 and thus generates fluorescent light, the generated fluorescent light hardly has influence on the reaction vessel 24. The detection vessel 55 is for temporarily accommodating the liquid under test, such as blood. Although not particularly shown, a seal member made of aluminum or the like is provided to cover all the vessels except the detection vessel 55. The detection vessel 55 has its side wall top formed with a notch 55a, through which the liquid under test is to be introduced. In addition, it has a narrowed lower portion such that it substantially regularly faces only the label solution vessel 54. A vertically extending engagement recess 56a is formed such that it corresponds to the notch 55a. Another engagement recess 56b is formed at a predetermined position adjacent the prism 12. The positioning of the prism 12 with respect to the optical axis of the optical system, can be attained by engaging together the two engagement recesses 56a and 56b with chuck pawls (not shown), for instance.

Of the diluting solution, stirring, multi-function and label solution vessels 51 to 54 the side wall 57 on the side of the reaction vessel 24 is inclined and has a shoulder 57a at an intermediate height position. Of the inclined side wall 57, the portion 57b on the lower side of the shoulder 57a regularly faces the optical waveguide body 11 with a slight gap provided relative thereto. The portion 57c of the wall 57 on the upper side of the shoulder 57a also serves as the side wall of the reaction vessel 24. The side wall 57d which opposes the inclined side wall 57 has an opposite inclination. Of course the side wall 57e of the reaction vessel 24 which opposes the side wall 57c has an opposite inclination to that of the optical waveguide body 11. The shoulder 57a and all the inclined side walls 57b to 57c, are equal in thickness to the bottom, thus permitting great reduction of deformation at the time of the molding. The inclination of each of the inclined walls 57b to 57e is set to about 3° with respect to the vertical plane, thus facilitating the die separation at the time of the molding. The optical waveguide body 11 has an inclination angle of about 9° to the vertical plane, and its surfaces formed by molding are formed to be like a mirror surface. Further, auxiliary walls 58a to 58f extending horizontally from the surface with the prism 12 formed thereon and have an equal thickness. Thus, it is possible to greatly reduce deformation at the time of the molding, and also touching of the prism 12 with fingers, hands, etc. can be prevented. Further, since the optical measurement apparatus has a large number of vessels formed in it, it naturally has a large number of side walls defining the individual vessels. Thus, the mechanical strength of the optical measurement apparatus as a whole is improved. In FIG. 20, the slight shoulder formed on the edge of the opening is for obtaining a reliable seal by the seal member.

Labeled B in FIG. 19 is a nozzle orbit. The nozzle is adapted to proceed right above the reaction vessel 24 and stirring, multi-function, label solution and detection vessels 52 to 55. The movement of the nozzle, which is necessary for the optical measurement, may be caused along the orbit B. The nozzle, however, has to be moved to be right above the diluting solution vessel 51. This movement may be caused in a considerably early stage in the optical measurement. Thus, to this end the nozzle is moved along an orbit other than the orbit B.

For carrying out normal fluorescent immunity measurement with the optical measurement apparatus of the above construction, a solution containing fluorescent label antibodies is preliminarily accommodated in the label solution vessel 54.

First, the seal member (not shown) is separated, and then the liquid under test, for instance blood, is poured into the detection vessel 55 by tilting a test tube containing the liquid with the edge of opening of the test tube engaged in the notch 55a. Then, the optical measurement apparatus is positioned by engaging the engagement recesses 56a and 56b with the chuck pawls (not shown). Subsequently, the nozzle (not shown) is moved to be right above the stirring and detection vessels 52 and 55 and then lowered for withdrawal of necessary quantities of the diluting solution and liquid under test. Then, the nozzle is raised and moved to be right above the stirring vessel 53, and then it is lowered for discharge of the diluting solution and liquid under test. In this state, the withdrawal and discharge are made by the nozzle repeatedly by a necessary number of times, thus attaining the stirring of the diluting solution and liquid under test.

After the above pre-treatment has been completed, the nozzle is caused to withdraw the diluted liquid under test n the stirring vessel 53, then raised, then moved to be right above the reaction vessel 53 and then lowered for discharging the diluted liquid under test. As a result, an antigen-antibody reaction is brought about between antibodies having been attached to the optical waveguide body 11 and antigens contained in the diluted liquid under test. After the antigen-antibody reaction has been carried out for a predetermined period of the, the nozzle is caused to withdraw all the liquid under test in the reaction vessel 24, then raised and then moved to a discarding section (not shown) for discharging the liquid under test. At this the, the nozzle is washed, if necessary. Afterwards, the nozzle is moved to be right above the label solution vessel 54, then lowered for withdrawal of the solution containing fluorescent label antibodies, then raised and then moved to be right above the reaction vessel 24. It is then lowered for discharge of the solution containing the fluorescent label antibodies. As a result, an antigen-antibody reaction is brought about between the antigens restrained in the neighborhood of the surface of the optical waveguide body 11 and the fluorescent label antibodies. With this antigen-antibody reaction, the fluorescent label antibodies are restrained in the neighborhood of the surface of the optical waveguide body 11. Thus, the label fluorescent material in the restrained fluorescent label antibodies is excited by the evanescent wave component to radiate a peculiar fluorescent light. Of course, the excitation light that has been introduced into the optical waveguide body 11 through the prism 12, is ultimately led to the light absorber vessel 25, and there is substantially no component returning toward the prism 12. In addition, there is substantially no influence of fluorescent light which is liable to be radiated from the label solution vessel 54. It is thus possible to determine the degree of the immunity reaction highly accurately according to the peculiar fluorescent light.

When making measurement of hepatitis label, cancer label, etc. by using the above optical measurement apparatus, a solution containing biotin label antibodies is preliminarily accommodated n the label solution vessel 54, and a solution containing fluorescent label avidin is accommodated in the multi-function vessel 53.

Figure 22:
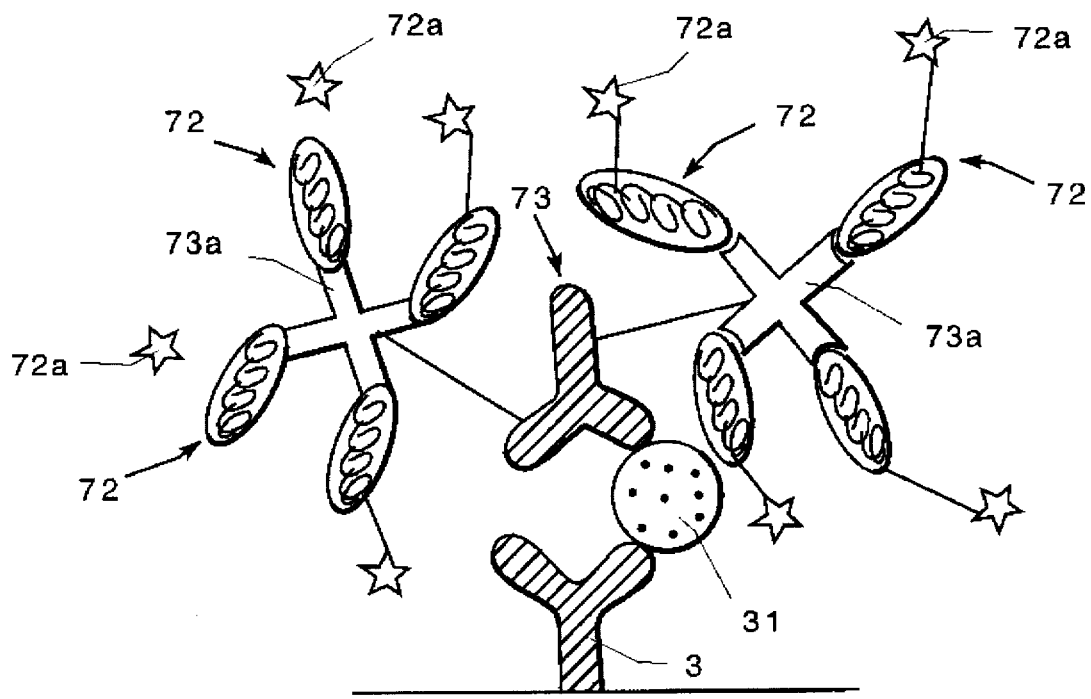
FIG. 22 is a schematic view showing a reaction mechanism using a biotin label antibodies and fluorescent label avidin.
Figure 23:
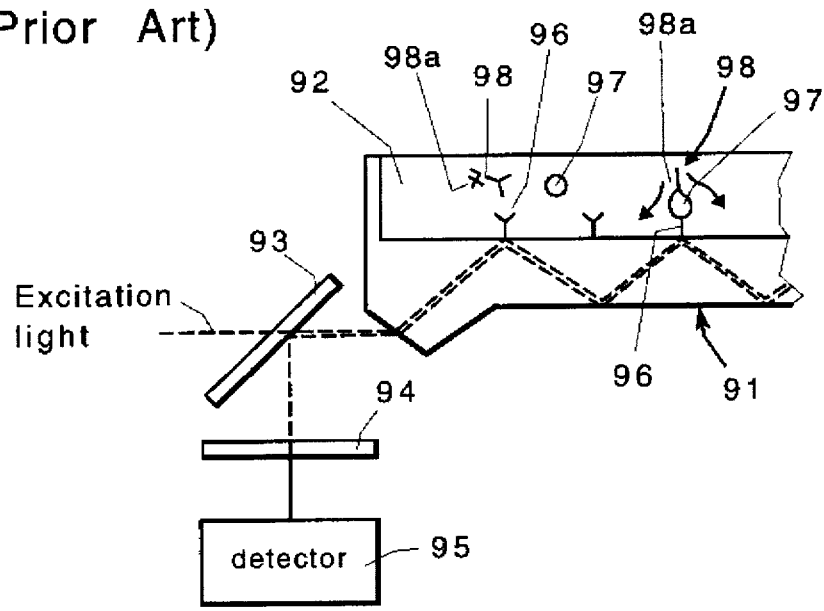
FIG. 23 is a schematic view showing a prior art optical measurement apparatus.

In this case, an antigen-antibody reaction is brought about between the antigens 31 contained in the liquid under test and antibodies 3 attached in advance to the optical waveguide body 11. Then, after discarding the liquid under test, the nozzle is moved to be right above the multi-function vessel 53, then lowered for withdrawal of the solution containing biotin label antibodies 73, then raised, then moved to be right above the reaction vessel 24 and then lowered for discharge of the solution containing the biotin label antibodies 73. As a result, an antigen-antibody reaction is brought about between the antigens 31 restrained in the neighborhood of the surface of the optical waveguide body 11 and the biotin label antibodies 73. Subsequently, the solution containing the biotin label antibodies 73 is withdrawn and discarded like the liquid under test. Then, the nozzle is brought to be right above the label solution vessel 54, then lowered for withdrawal of the solution containing the fluorescent label avidin 72, then raised, then moved to be right above the reaction vessel 24 and then lowered for discharge of the solution containing the fluorescent label avidin 72. As a result, biotin 73a restrained in the neighborhood of the surface of the optical waveguide body 11 and the fluorescent label avidin 72 are coupled together by the antigen-antibody reaction noted above. As a result of this coupling, the fluorescent label avidin 72 is restrained in the neighborhood of the surface of the optical waveguide body 11. The label fluorescent material 72a in the restrained fluorescent label avidin 72 thus is excited by the evanescent wave component to radiate peculiar fluorescent light. With the coupling of the biotin 73a and avidin 72, a sufficient amount of fluorescent light can be radiated, because the amount of label fluorescent material that is restrained in the neighborhood of the surface of the optical guide body 11 is as much as several times (i.e., 5 to 10 times) the amount of the label fluorescent material restrained by the fluorescent label antibodies, as shown in FIG. 22. On the basis of this fluorescent light, the optical measurement can be attained.

The above embodiments of the invention are by no means limitative. For example, it is possible to attach antigens or hapten, instead of the antibodies 3, to the optical waveguide body 11. Also, the prism 12 for introducing excitation light into the optical waveguide body 11, may have other shapes than in the above embodiments, for instance a symmetrical wedge-like shape. Further, using fluorescent light, scattering, polarization, etc., it is possible to measure changes in optical characteristics stemming from other coupling reactions than the antigen-antibody reaction, catalytic reactions due to enzymes, etc. Further, it is possible to form some of the plurality of side walls defining the plurality of vessels to have a smaller height than the other side walls. Various further changes and modifications are possible without departing from the gist of the invention.

POSSIBILITY OF INDUSTRIAL UTILIZATION

Since the invention permits measurement of optical characteristics of the neighborhood of an optical waveguide surface depending on an antigen-antibody reaction or the like according to the evanescent wave component, it is extensively applicable as optical measurement apparatuses for various medical diagnosis purposes.

What is claimed is:

1. An apparatus for use in an optical measurement assembly, said apparatus comprising a plurality of vessels (21 to 24, 51 to 55) formed together as a monolithic molding, at least one of said vessels being a reaction vessel (24), said reaction vessel (24) facing at least one other vessel along a facing side wall of said monolithic molding, the facing side wall of said reaction vessel also being an optical waveguide (1) in said apparatus.

2. The apparatus according to claim 1, wherein antigens, antibodies or hapten are attached to at least one side surface of said optical waveguide (1).

3. The apparatus according to claim 1, wherein said optical waveguide (1) has an inclined form such that said reaction vessel (24) has a bottom which is narrower than an opened top of said vessel.

4. The apparatus according to claim 1, wherein said reaction vessel is dimensioned and arranged for a treatment of a substance and wherein there are a plurality of vessels other than said reaction vessel formed in said monolithic molding, and at least one of said plurality of other vessels is a pre-treatment vessel (21 to 24, 51 to 54).

5. The apparatus according to claim 4, wherein there are a plurality of pre-treatment vessels (21 to 24, 51 to 54) which said plurality of pre-treatment vessels include a reagent vessel (54) and/or a diluting solution vessel (51).

6. The apparatus according to claim 5, wherein one of said pre-treatment vessels is a reagent vessel (54) for storing a fluorescent material and does not share said facing side wall of said reaction vessel (24).

7. The apparatus according to claim 5, which further comprises a seal (6) which covers at least one of said reagent vessel (54) and said diluting solution vessel (51).

8. The apparatus according claim 2, wherein said optical waveguide (1) has a light incidence/emission prism (12) provided at one end for introducing excitation light into it in order for the excitation light to be propagated while being totally reflected and also for emitting signal light containing optical measurement information, a light absorber storing vessel (25) being disposed such as to correspond to the other end of said optical waveguide (1).

9. The apparatus according to claim 1 wherein said optical waveguide (1) has a light incidence/emission prism (12) provided at one end for introducing excitation light into it in order for the excitation light to be propagated while being totally reflected and also for emitting signal light containing optical measurement information, said optical waveguide (1) also being formed with a total reflection prism (16) provided at the other end for emitting excitation light in a direction at a predetermined angle with respect to an optical axis of said optical waveguide (1).

10. The apparatus according to claim 1, wherein said optical waveguide (1) has a light incidence/emission prism (1) provided at an end thereof for introducing excitation light into it in order for the excitation light to be propagated while being totally reflected and also emitting signal light containing optical measurement information, light penetration blocking means (27) for blocking light penetration, said light penetration blocking means being provided in a predetermined area adjacent an excitation light introduction area of said light incidence/emission prism (12).

11. The apparatus according to claim 2, wherein a side portion of said reaction vessel (24) that extends substantially at right angles to said optical waveguide (1), and that is positioned on an excitation light introduction side of said optical waveguide (1) and/or on a side extending substantially parallel to said optical waveguide (1) is coated with a black paint (24b, 24c).

12. The apparatus according to claim 1, which further comprises a light detector (5, 46) for detecting signal light emitted from said optical waveguide (1) and an analyzer (50) for analyzing immunity reactions according to a detection signal from said light detector (5, 46).

13. The apparatus according to claim 1 wherein said optical waveguide (1) has a light incidence/emission prism (1) provided at an end thereof for introducing excitation light into it in order for the excitation light to be propagated while being totally reflected and also emitting signal light containing optical measurement information.

14. The apparatus according to claim 1 wherein said facing side wall includes an upper portion and a lower portion, the lower portion includes two partitioning wall sections which branch off from one end of said upper portion, a first of said two partitioning wall sections being inclined away from said upper portion and toward an opposite side wall of said reaction vessel so as to form a space between said two partitioning wall sections.

15. The apparatus according to claim 14 wherein said first partitioning wall section is the optical waveguide and thus has flat, opposite surfaces for transmitting light in a totally reflected manner.

16. An apparatus for use in an optical measurement assembly, said apparatus comprising a plurality of vessels formed together as a monolithic unit, at least one of said vessels being a reaction vessel, said reaction vessel facing at least one other vessel along a facing side wall of said monolithic unit, the facing side wall of said reaction vessel being an optical waveguide in said apparatus for optical measurement wherein said optical waveguide has a light incidence/emission prism provided at one end for introducing excitation light into it in order for the excitation light to be propagated while being totally reflected and also for emitting signal light containing optical measurement information, and a light absorber storing vessel being disposed such as to correspond to the other end of said optical waveguide.

17. An apparatus for use in an optical measurement assembly, said apparatus comprising a plurality of vessels formed together as a monolithic molding, at least one of said vessels being a reaction vessel, said reaction vessel facing at least one other vessel along a facing side wall of said monolithic molding, the facing side wall of said reaction vessel being an optical waveguide in said apparatus for optical measurement, wherein a side portion of said reaction vessel that extends substantially at right angles to said optical waveguide and that is positioned on an excitation light introduction side of said optical waveguide and/or on a side extending substantially parallel to said optical waveguide is coated with a black paint.

18. An apparatus according to claim 1 wherein said facing side wall has flat, opposite surfaces for transmitting light in a totally reflected manner.

* * * * *